US005767261A

United States Patent [19]

Wingate et al.

[11] Patent Number: 5,767,261

[45] Date of Patent: Jun. 16, 1998

[54] LEPIDOPTERAN GABA GATED CHLORIDE CHANNEL AND NUCLEIC ACIDS ENCODING SUBUNITS THEREOF

[75] Inventors: Vincent Wingate, Chapel Hill; Mark Wolff, Cary, both of N.C.

[73] Assignee: Rhone -Poulenc AG Company, Research Triangle Park, N.C.

[21] Appl. No.: 554,659

[22] Filed: Nov. 8, 1995

[51] Int. Cl.[6] .......................... C07K 14/705; C12N 5/10; C12N 15/12

[52] U.S. Cl. ........................ 536/23.5; 536/23.1; 530/350; 435/325; 435/348; 435/254.11; 435/69.1; 435/320.1; 435/252.3

[58] Field of Search ................................. 536/23.1, 23.5; 530/350; 435/252.3, 254.11, 320.1, 240.2, 69.1, 325, 348

[56] References Cited

U.S. PATENT DOCUMENTS 5,487,976 1/1996 Soderlund et al. .................... 435/7.21

FOREIGN PATENT DOCUMENTS

93/07161 4/1993 WIPO .

OTHER PUBLICATIONS

Anthony et al., "GABA receptor molecules of insects", in Comparative Molecular Neurobiology, Y. Pichon, Ed., Birkhauser Verlag (Basel, Switzerland), pp. 172–209, 1993.

Darlison et al., GABAA receptor subtypes: which, where and why?, Seminars Neurosci., 7: 115–126, 1995.

Malecot et al, "GABA receptors in the nervous system of an instect, Periplaneta americana", in GABA–B Receptrors in Mammalian Function, N. Bowery et al., Eds, John Wiley and Sons (New York), p. 431, 1990.

Chen et al., Cloning and functional expression of a Drosophila gamma–aminobutyric acid receptor, Proc. Natl. Acad. Sci. USA, 91: 6069–6073, Jun. 1994.

Ffrench–Constant et al., Molecular cloning and transformation of cyclodiene resistance in Drosophila: An invertebrate gamma–aminobutyric acid subtype A receptor locus, Proc. Natl. Acad. Sci. USA, 88: 7209–7213, Aug. 1991.

Lunt, GABA and GABA receptors in inverebrates, Seminars Neurosci., 3(3): 251–258, Jun. 1991.

Miyazaki et al., DNA sequence and site of mutation of the GABA receptor of cyclodiene–resistant red flour beetle, Tribolium castaneum, Comp. Boichem. Physiol., 111 B(3): 399–406, 1995.

Shotkoski et al., Functional expression of insecticide–resistant GABA receptors from the mosquito Aedes aegypti, Insect Mol. Biol., 3(4): 283–287, 1994.

Thompson et al., Cloning and sequencing of the cyclodiene insecticide resistance gene from the yellow fever mosquito aedes aegypti, FEBS, 325(3): 187–190, Jul. 1993.

Marullo et al., Expression of human B1 and B2 adrenergic receptors in E. coli as a new tool for ligand screening, Bio/Technology, 7:923–927, Sep. 1989.

*Primary Examiner*—Stephen Walsh
*Assistant Examiner*—Claire M. Kaufman
*Attorney, Agent, or Firm*—Scully, Scott, Murphy & Presser

[57] ABSTRACT

The present invention provides isolated nucleic acids encoding lepidopteran gamma aminobutyric acid (GABA) gated chloride channels. In a preferred embodiment, the nucleic acids encoding lepidopteran GABA gated chloride channels are isolatable from *Heliothis virescens*. The invention further provides recombinant lepidopteran GABA gated chloride channels and methods for identifying agonists and antagonists to a lepidopteran GABA gated chloride channels.

17 Claims, 7 Drawing Sheets

Polylinker I: 3.4/XhoI. XbaI. BglII. Asp718I. KpnI. Ecl136II. SacI. EcoRI. XmaI. SmaI. EagI. StuI. NotI. PacI.

Polylinker I: 0.5/XhoI.EcoRV. BamHI. SpeI*.XbaI*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1657 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 115..1581

( x i ) SEQUENCE DESCRIPTION: SEQ ID NO:1:

```
GAATTCGGCA CGAGGACGCC TGAGGGCCTG TAAGAACACG CCAGTCCGGC CGGCACGGTG        60

ATACGCGGCT GCCGGCAGCC AGCGTCCGCA AGGGCGCACG CGGACCTGCA AAAC ATG         117
                                                              Met
                                                               1

CAT ACG AGC CGT CCG CGC GGC GTG CAC AGC ATC GCG CTA GTG CTG TCT         165
His Thr Ser Arg Pro Arg Gly Val His Ser Ile Ala Leu Val Leu Ser
          5                  10                  15

CTC GCG ATT GCC TGG TTA CCT CAT GCT GAC CAT GCC GCG GGA GCG GGA         213
Leu Ala Ile Ala Trp Leu Pro His Ala Asp His Ala Ala Gly Ala Gly
         20                  25                  30

GGA GGG GGA ATG TTT GGT GAC GTC AAT ATC TCA GCC ATT TTG GAT TCG         261
Gly Gly Gly Met Phe Gly Asp Val Asn Ile Ser Ala Ile Leu Asp Ser
     35                  40                  45

CTA AGT GTA AGC TAC GAC AAA AGA GTG AGG CCG AAC TAT GGA GGA CCG         309
Leu Ser Val Ser Tyr Asp Lys Arg Val Arg Pro Asn Tyr Gly Gly Pro
 50                  55                  60                  65

CCA GTG GAT GTG GGA GTC AAC ATG TAC GTG CTC TCC ATC AGC TCC TTA         357
Pro Val Asp Val Gly Val Asn Met Tyr Val Leu Ser Ile Ser Ser Leu
                 70                  75                  80

TCT GAA GTG AAA ATG GAT TTC ACC CTG GAT TTC TAC TTC AGA CAA TTT         405
Ser Glu Val Lys Met Asp Phe Thr Leu Asp Phe Tyr Phe Arg Gln Phe
             85                  90                  95

TGG ACA GAC CCC AGG CTT GCT TAC AAA AAA AGC ACG GGT GTG GAG ACT         453
Trp Thr Asp Pro Arg Leu Ala Tyr Lys Lys Ser Thr Gly Val Glu Thr
        100                 105                 110

CTG TCC GTC GGC TCG GAA TTT ATT AGA AAC ATA TGG GTA CCC GAC ACC         501
Leu Ser Val Gly Ser Glu Phe Ile Arg Asn Ile Trp Val Pro Asp Thr
    115                 120                 125

TTC TTT GTT AAC GAA AAA CAG TCA TAT TTC CAC ATA GCT ACT ACA AGC         549
Phe Phe Val Asn Glu Lys Gln Ser Tyr Phe His Ile Ala Thr Thr Ser
130                 135                 140                 145

AAC GAA TTC ATA CGC ATT CAT CAT TCT GGA TCT ATT ACT AGG AGT ATA         597
Asn Glu Phe Ile Arg Ile His His Ser Gly Ser Ile Thr Arg Ser Ile
                150                 155                 160

AGA CTG ACT ATC ACC GCT TCT TGT CCG ATG GAT TTG CAG TAT TTT CCG         645
Arg Leu Thr Ile Thr Ala Ser Cys Pro Met Asp Leu Gln Tyr Phe Pro
            165                 170                 175

ATG GAC CGT CAA TTA TGC AAT ATT GAA ATC GAA AGT TTT GGC TAC ACC         693
Met Asp Arg Gln Leu Cys Asn Ile Glu Ile Glu Ser Phe Gly Tyr Thr
        180                 185                 190

ATG CGG GAC ATC CGA TAC AAG TGG AAT GAG GGG CCC AAC TCA GTG GGT         741
Met Arg Asp Ile Arg Tyr Lys Trp Asn Glu Gly Pro Asn Ser Val Gly
```

-continued

```
     195                      200                      205

GTG TCG AGC GAA GTG TCT TTG CCG CAA TTC AAG GTG CTG GGC CAC CGG      789
Val Ser Ser Glu Val Ser Leu Pro Gln Phe Lys Val Leu Gly His Arg
210                 215                 220                 225

CAG CGG GCC ATG GAG ATT TCT CTT ACG ACA GGA AAC TAC TCT CGT CTG      837
Gln Arg Ala Met Glu Ile Ser Leu Thr Thr Gly Asn Tyr Ser Arg Leu
                230                 235                 240

GCA TGT GAA ATT CAA TTT GTA GGC TCG ATG GGA TAC TAT TTA ATT CAG      885
Ala Cys Glu Ile Gln Phe Val Gly Ser Met Gly Tyr Tyr Leu Ile Gln
            245                 250                 255

ATT TAT ATT CCG TCT GGC CTA ATT GTC ATT ATA TCT TGG GTA TCA TTT      933
Ile Tyr Ile Pro Ser Gly Leu Ile Val Ile Ile Ser Trp Val Ser Phe
        260                 265                 270

TGG TTG AAT CGA AAT GCG ACA CCT GCA AGG GTA TCA CTA GGT GTC ACA      981
Trp Leu Asn Arg Asn Ala Thr Pro Ala Arg Val Ser Leu Gly Val Thr
    275                 280                 285

ACT GTA TTG ACG ATG ACG ACG CTC ATG TCG TCC ACG AAT GCG GCT CTG     1029
Thr Val Leu Thr Met Thr Thr Leu Met Ser Ser Thr Asn Ala Ala Leu
290                 295                 300                 305

CCC AAG ATC TCA TAT GTC AAG TCC ATC GAT GTC TAT CTG GGA ACT TGT     1077
Pro Lys Ile Ser Tyr Val Lys Ser Ile Asp Val Tyr Leu Gly Thr Cys
                310                 315                 320

TTC GTC ATG GTC TTC ACC AGT TTA CTA GAA TAT GCC ACG GTT GGC TAT     1125
Phe Val Met Val Phe Thr Ser Leu Leu Glu Tyr Ala Thr Val Gly Tyr
            325                 330                 335

ATG GCG AAA AGG ATA CAG ATG AGG AAA CAA AGA TTC ACT GCT GTT CAA     1173
Met Ala Lys Arg Ile Gln Met Arg Lys Gln Arg Phe Thr Ala Val Gln
        340                 345                 350

AAA ATG CAA ATA GAT GGT CCT CCA GGG TCA GCT GAG CCT ATC CCC CCA     1221
Lys Met Gln Ile Asp Gly Pro Pro Gly Ser Ala Glu Pro Ile Pro Pro
    355                 360                 365

CCG AGG ACC AGC ACC CTA TCT AGG CCA CCA CCT AGC CGA TTA TCG GAG     1269
Pro Arg Thr Ser Thr Leu Ser Arg Pro Pro Pro Ser Arg Leu Ser Glu
370                 375                 380                 385

GTT CGG TTC AAA GTT CAC GAT CCG AAG GCA TAT TCT AAA GGC GGT ACT     1317
Val Arg Phe Lys Val His Asp Pro Lys Ala Tyr Ser Lys Gly Gly Thr
                390                 395                 400

TTA GAA AAC ACT ATC AAT GGG GCT CGG GGC CAG CCA GGA CCT GCT CCA     1365
Leu Glu Asn Thr Ile Asn Gly Ala Arg Gly Gln Pro Gly Pro Ala Pro
            405                 410                 415

CCG GCA GAC GAA GAA GCT GGA CCA CCT CCG CAT CTC GTT CAT GCT TTC     1413
Pro Ala Asp Glu Glu Ala Gly Pro Pro Pro His Leu Val His Ala Phe
        420                 425                 430

CAA GGT ATC AAC AAA CTG CTC GGC ACG ACC CCC TCG GAC ATC GAC AAG     1461
Gln Gly Ile Asn Lys Leu Leu Gly Thr Thr Pro Ser Asp Ile Asp Lys
    435                 440                 445

TAC TCG CGC ATC GTG TTC CCC GTC TGC TGC GTT TGC TTT AAC CTT ATG     1509
Tyr Ser Arg Ile Val Phe Pro Val Cys Cys Val Cys Phe Asn Leu Met
450                 455                 460                 465

TAC TGG ATC ATT TAC CTT CAC GTG TCT GAC GTC GTG GCT GAT GAC TTG     1557
Tyr Trp Ile Ile Tyr Leu His Val Ser Asp Val Val Ala Asp Asp Leu
                470                 475                 480

GTA CTA CTA GGC GAA GAA AAT TGAATTCTCT TTAACTATAC CGGACTTGTT        1608
Val Leu Leu Gly Glu Glu Asn
            485

TTAACTTAGG GTGCTTATGA TCAACCATCC ATCAGGTTTC GGTAAAGTT               1657
```

( 2 ) INFORMATION FOR SEQ ID NO:2:

( i ) SEQUENCE CHARACTERISTICS:

-continued ( A ) LENGTH: 488 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met His Thr Ser Arg Pro Arg Gly Val His Ser Ile Ala Leu Val Leu
1 5 10 15

Ser Leu Ala Ile Ala Trp Leu Pro His Ala Asp His Ala Ala Gly Ala
20 25 30

Gly Gly Gly Gly Met Phe Gly Asp Val Asn Ile Ser Ala Ile Leu Asp
35 40 45

Ser Leu Ser Val Ser Tyr Asp Lys Arg Val Arg Pro Asn Tyr Gly Gly
50 55 60

Pro Pro Val Asp Val Gly Val Asn Met Tyr Val Leu Ser Ile Ser Ser
65 70 75 80

Leu Ser Glu Val Lys Met Asp Phe Thr Leu Asp Phe Tyr Phe Arg Gln
85 90 95

Phe Trp Thr Asp Pro Arg Leu Ala Tyr Lys Lys Ser Thr Gly Val Glu
100 105 110

Thr Leu Ser Val Gly Ser Glu Phe Ile Arg Asn Ile Trp Val Pro Asp
115 120 125

Thr Phe Phe Val Asn Glu Lys Gln Ser Tyr Phe His Ile Ala Thr Thr
130 135 140

Ser Asn Glu Phe Ile Arg Ile His His Ser Gly Ser Ile Thr Arg Ser
145 150 155 160

Ile Arg Leu Thr Ile Thr Ala Ser Cys Pro Met Asp Leu Gln Tyr Phe
165 170 175

Pro Met Asp Arg Gln Leu Cys Asn Ile Glu Ile Glu Ser Phe Gly Tyr
180 185 190

Thr Met Arg Asp Ile Arg Tyr Lys Trp Asn Glu Gly Pro Asn Ser Val
195 200 205

Gly Val Ser Ser Glu Val Ser Leu Pro Gln Phe Lys Val Leu Gly His
210 215 220

Arg Gln Arg Ala Met Glu Ile Ser Leu Thr Thr Gly Asn Tyr Ser Arg
225 230 235 240

Leu Ala Cys Glu Ile Gln Phe Val Gly Ser Met Gly Tyr Tyr Leu Ile
245 250 255

Gln Ile Tyr Ile Pro Ser Gly Leu Ile Val Ile Ile Ser Trp Val Ser
260 265 270

Phe Trp Leu Asn Arg Asn Ala Thr Pro Ala Arg Val Ser Leu Gly Val
275 280 285

Thr Thr Val Leu Thr Met Thr Thr Leu Met Ser Ser Thr Asn Ala Ala
290 295 300

Leu Pro Lys Ile Ser Tyr Val Lys Ser Ile Asp Val Tyr Leu Gly Thr
305 310 315 320

Cys Phe Val Met Val Phe Thr Ser Leu Leu Glu Tyr Ala Thr Val Gly
325 330 335

Tyr Met Ala Lys Arg Ile Gln Met Arg Lys Gln Arg Phe Thr Ala Val
340 345 350

Gln Lys Met Gln Ile Asp Gly Pro Pro Gly Ser Ala Glu Pro Ile Pro
355 360 365

Pro Pro Arg Thr Ser Thr Leu Ser Arg Pro Pro Pro Ser Arg Leu Ser
370 375 380

-continued

```
Glu Val Arg Phe Lys Val His Asp Pro Lys Ala Tyr Ser Lys Gly Gly
385                 390                 395                 400

Thr Leu Glu Asn Thr Ile Asn Gly Ala Arg Gly Gln Pro Gly Pro Ala
                405                 410                 415

Pro Pro Ala Asp Glu Glu Ala Gly Pro Pro Pro His Leu Val His Ala
            420                 425                 430

Phe Gln Gly Ile Asn Lys Leu Leu Gly Thr Thr Pro Ser Asp Ile Asp
        435                 440                 445

Lys Tyr Ser Arg Ile Val Phe Pro Val Cys Cys Val Cys Phe Asn Leu
    450                 455                 460

Met Tyr Trp Ile Ile Tyr Leu His Val Ser Asp Val Val Ala Asp Asp
465                 470                 475                 480

Leu Val Leu Leu Gly Glu Glu Asn
                485
```

( 2 ) INFORMATION FOR SEQ ID NO:3:

( i ) SEQUENCE CHARACTERISTICS:
( A ) LENGTH: 1657 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 115..1581

( x i ) SEQUENCE DESCRIPTION: SEQ ID NO:3:

```
GAATTCGGCA CGAGGACGCC TGAGGGCCTG TAAGAACACG CCAGTCCGGC CGGCACGGTG      60

ATACGCGGCT GCCGGCAGCC AGCGTCCGCA AGGGCGCACG CGGACCTGCA AAAC ATG       117
                                                            Met
                                                              1

CAT ACG AGC CGT CCG CGC GGC GTG CAC AGC ATC GCG CTA GTG CTG TCT      165
His Thr Ser Arg Pro Arg Gly Val His Ser Ile Ala Leu Val Leu Ser
              5                  10                  15

CTC GCG ATT GCC TGG TTA CCT CAT GCT GAC CAT GCC GCG GGA GCG GGA      213
Leu Ala Ile Ala Trp Leu Pro His Ala Asp His Ala Ala Gly Ala Gly
         20                  25                  30

GGA GGG GGA ATG TTT GGT GAC GTC AAT ATC TCA GCC ATT TTG GAT TCG      261
Gly Gly Gly Met Phe Gly Asp Val Asn Ile Ser Ala Ile Leu Asp Ser
     35                  40                  45

CTA AGT GTA AGC TAC GAC AAA AGA GTG AGG CCG AAC TAT GGA GGA CCG      309
Leu Ser Val Ser Tyr Asp Lys Arg Val Arg Pro Asn Tyr Gly Gly Pro
 50                  55                  60                  65

CCA GTG GAT GTG GGA GTC AAC ATG TAC GTG CTC TCC ATC AGC TCC TTA      357
Pro Val Asp Val Gly Val Asn Met Tyr Val Leu Ser Ile Ser Ser Leu
                 70                  75                  80

TCT GAA GTG AAA ATG GAT TTC ACC CTG GAT TTC TAC TTC AGA CAA TTT      405
Ser Glu Val Lys Met Asp Phe Thr Leu Asp Phe Tyr Phe Arg Gln Phe
             85                  90                  95

TGG ACA GAC CCC AGG CTT GCT TAC AAA AAA AGC ACG GGT GTG GAG ACT      453
Trp Thr Asp Pro Arg Leu Ala Tyr Lys Lys Ser Thr Gly Val Glu Thr
        100                 105                 110

CTG TCC GTC GGC TCG GAA TTT ATT AGA AAC ATA TGG GTA CCC GAC ACC      501
Leu Ser Val Gly Ser Glu Phe Ile Arg Asn Ile Trp Val Pro Asp Thr
    115                 120                 125

TTC TTT GTT AAC GAA AAA CAG TCA TAT TTC CAC ATA GCT ACT ACA AGC      549
Phe Phe Val Asn Glu Lys Gln Ser Tyr Phe His Ile Ala Thr Thr Ser
130                 135                 140                 145
```

-continued

```
AAC GAA TTC ATA CGC ATT CAT CAT TCT GGA TCT ATT ACT AGG AGT ATA     597
Asn Glu Phe Ile Arg Ile His His Ser Gly Ser Ile Thr Arg Ser Ile
                150                 155                 160

AGA CTG ACT ATC ACC GCT TCT TGT CCG ATG GAT TTG CAG TAT TTT CCG     645
Arg Leu Thr Ile Thr Ala Ser Cys Pro Met Asp Leu Gln Tyr Phe Pro
            165                 170                 175

ATG GAC CGT CAA TTA TGC AAT ATT GAA ATC GAA AGT TTT GGC TAC ACC     693
Met Asp Arg Gln Leu Cys Asn Ile Glu Ile Glu Ser Phe Gly Tyr Thr
        180                 185                 190

ATG CGG GAC ATC CGA TAC AAG TGG AAT GAG GGG CCC AAC TCA GTG GGT     741
Met Arg Asp Ile Arg Tyr Lys Trp Asn Glu Gly Pro Asn Ser Val Gly
    195                 200                 205

GTG TCG AGC GAA GTG TCT TTG CCG CAA TTC AAG GTG CTG GGC CAC CGG     789
Val Ser Ser Glu Val Ser Leu Pro Gln Phe Lys Val Leu Gly His Arg
210                 215                 220                 225

CAG CGG GCC ATG GAG ATT TCT CTT ACG ACA GGA AAC TAC TCT CGT CTG     837
Gln Arg Ala Met Glu Ile Ser Leu Thr Thr Gly Asn Tyr Ser Arg Leu
                230                 235                 240

GCA TGT GAA ATT CAA TTT GTA GGC TCG ATG GGA TAC TAT TTA ATT CAG     885
Ala Cys Glu Ile Gln Phe Val Gly Ser Met Gly Tyr Tyr Leu Ile Gln
            245                 250                 255

ATT TAT ATT CCG TCT GGC CTA ATT GTC ATT ATA TCT TGG GTA TCA TTT     933
Ile Tyr Ile Pro Ser Gly Leu Ile Val Ile Ile Ser Trp Val Ser Phe
        260                 265                 270

TGG TTG AAT CGA AAT GCG ACA CCT GCA AGG GTA GCA CTA GGT GTC ACA     981
Trp Leu Asn Arg Asn Ala Thr Pro Ala Arg Val Ala Leu Gly Val Thr
    275                 280                 285

ACT GTA TTG ACG ATG ACG ACG CTC ATG TCG TCC ACG AAT GCG GCT CTG    1029
Thr Val Leu Thr Met Thr Thr Leu Met Ser Ser Thr Asn Ala Ala Leu
290                 295                 300                 305

CCC AAG ATC TCA TAT GTC AAG TCC ATC GAT GTC TAT CTG GGA ACT TGT    1077
Pro Lys Ile Ser Tyr Val Lys Ser Ile Asp Val Tyr Leu Gly Thr Cys
                310                 315                 320

TTC GTC ATG GTC TTC ACC AGT TTA CTA GAA TAT GCC ACG GTT GGC TAT    1125
Phe Val Met Val Phe Thr Ser Leu Leu Glu Tyr Ala Thr Val Gly Tyr
            325                 330                 335

ATG GCG AAA AGG ATA CAG ATG AGG AAA CAA AGA TTC ACT GCT GTT CAA    1173
Met Ala Lys Arg Ile Gln Met Arg Lys Gln Arg Phe Thr Ala Val Gln
        340                 345                 350

AAA ATG CAA ATA GAT GGT CCT CCA GGG TCA GCT GAG CCT ATC CCC CCA    1221
Lys Met Gln Ile Asp Gly Pro Pro Gly Ser Ala Glu Pro Ile Pro Pro
    355                 360                 365

CCG AGG ACC AGC ACC CTA TCT AGG CCA CCA CCT AGC CGA TTA TCG GAG    1269
Pro Arg Thr Ser Thr Leu Ser Arg Pro Pro Pro Ser Arg Leu Ser Glu
370                 375                 380                 385

GTT CGG TTC AAA GTT CAC GAT CCG AAG GCA TAT TCT AAA GGC GGT ACT    1317
Val Arg Phe Lys Val His Asp Pro Lys Ala Tyr Ser Lys Gly Gly Thr
                390                 395                 400

TTA GAA AAC ACT ATC AAT GGG GCT CGG GGC CAG CCA GGA CCT GCT CCA    1365
Leu Glu Asn Thr Ile Asn Gly Ala Arg Gly Gln Pro Gly Pro Ala Pro
            405                 410                 415

CCG GCA GAC GAA GAA GCT GGA CCA CCT CCG CAT CTC GTT CAT GCT TTC    1413
Pro Ala Asp Glu Glu Ala Gly Pro Pro Pro His Leu Val His Ala Phe
        420                 425                 430

CAA GGT ATC AAC AAA CTG CTC GGC ACG ACC CCC TCG GAC ATC GAC AAG    1461
Gln Gly Ile Asn Lys Leu Leu Gly Thr Thr Pro Ser Asp Ile Asp Lys
    435                 440                 445

TAC TCG CGC ATC GTG TTC CCC GTC TGC TGC GTT TGC TTT AAC CTT ATG    1509
Tyr Ser Arg Ile Val Phe Pro Val Cys Cys Val Cys Phe Asn Leu Met
450                 455                 460                 465
```

-continued

TAC TGG ATC ATT TAC CTT CAC GTG TCT GAC GTC GTG GCT GAT GAC TTG 1557
Tyr Trp Ile Ile Tyr Leu His Val Ser Asp Val Val Ala Asp Asp Leu
470 475 480

GTA CTA CTA GGC GAA GAA AAT TGAATTCTCT TTAACTATAC CGGACTTGTT 1608
Val Leu Leu Gly Glu Glu Asn
485

TTAACTTAGG GTGCTTATGA TCAACCATCC ATCAGGTTTC GGTAAAGTT 1657

( 2 ) INFORMATION FOR SEQ ID NO:4:

( i ) SEQUENCE CHARACTERISTICS:
( A ) LENGTH: 488 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met His Thr Ser Arg Pro Arg Gly Val His Ser Ile Ala Leu Val Leu
1 5 10 15

Ser Leu Ala Ile Ala Trp Leu Pro His Ala Asp His Ala Ala Gly Ala
20 25 30

Gly Gly Gly Gly Met Phe Gly Asp Val Asn Ile Ser Ala Ile Leu Asp
35 40 45

Ser Leu Ser Val Ser Tyr Asp Lys Arg Val Arg Pro Asn Tyr Gly Gly
50 55 60

Pro Pro Val Asp Val Gly Val Asn Met Tyr Val Leu Ser Ile Ser Ser
65 70 75 80

Leu Ser Glu Val Lys Met Asp Phe Thr Leu Asp Phe Tyr Phe Arg Gln
85 90 95

Phe Trp Thr Asp Pro Arg Leu Ala Tyr Lys Lys Ser Thr Gly Val Glu
100 105 110

Thr Leu Ser Val Gly Ser Glu Phe Ile Arg Asn Ile Trp Val Pro Asp
115 120 125

Thr Phe Phe Val Asn Glu Lys Gln Ser Tyr Phe His Ile Ala Thr Thr
130 135 140

Ser Asn Glu Phe Ile Arg Ile His His Ser Gly Ser Ile Thr Arg Ser
145 150 155 160

Ile Arg Leu Thr Ile Thr Ala Ser Cys Pro Met Asp Leu Gln Tyr Phe
165 170 175

Pro Met Asp Arg Gln Leu Cys Asn Ile Glu Ile Glu Ser Phe Gly Tyr
180 185 190

Thr Met Arg Asp Ile Arg Tyr Lys Trp Asn Glu Gly Pro Asn Ser Val
195 200 205

Gly Val Ser Ser Glu Val Ser Leu Pro Gln Phe Lys Val Leu Gly His
210 215 220

Arg Gln Arg Ala Met Glu Ile Ser Leu Thr Thr Gly Asn Tyr Ser Arg
225 230 235 240

Leu Ala Cys Glu Ile Gln Phe Val Gly Ser Met Gly Tyr Tyr Leu Ile
245 250 255

Gln Ile Tyr Ile Pro Ser Gly Leu Ile Val Ile Ile Ser Trp Val Ser
260 265 270

Phe Trp Leu Asn Arg Asn Ala Thr Pro Ala Arg Val Ala Leu Gly Val
275 280 285

Thr Thr Val Leu Thr Met Thr Thr Leu Met Ser Ser Thr Asn Ala Ala
290 295 300

Leu Pro Lys Ile Ser Tyr Val Lys Ser Ile Asp Val Tyr Leu Gly Thr

-continued

| | | | | | | | | | | | | | | | |
|---|---|---|---|---|---|---|---|---|---|---|---|---|---|---|---|
| 305 | | | | | 310 | | | | | 315 | | | | | 320 |
| Cys | Phe | Val | Met | Val | Phe | Thr | Ser | Leu | Leu | Glu | Tyr | Ala | Thr | Val | Gly |
| | | | | 325 | | | | | 330 | | | | | 335 | |
| Tyr | Met | Ala | Lys | Arg | Ile | Gln | Met | Arg | Lys | Gln | Arg | Phe | Thr | Ala | Val |
| | | | 340 | | | | | 345 | | | | | 350 | | |
| Gln | Lys | Met | Gln | Ile | Asp | Gly | Pro | Pro | Gly | Ser | Ala | Glu | Pro | Ile | Pro |
| | | 355 | | | | | 360 | | | | | 365 | | | |
| Pro | Pro | Arg | Thr | Ser | Thr | Leu | Ser | Arg | Pro | Pro | Pro | Ser | Arg | Leu | Ser |
| | 370 | | | | | 375 | | | | | 380 | | | | |
| Glu | Val | Arg | Phe | Lys | Val | His | Asp | Pro | Lys | Ala | Tyr | Ser | Lys | Gly | Gly |
| 385 | | | | | 390 | | | | | 395 | | | | | 400 |
| Thr | Leu | Glu | Asn | Thr | Ile | Asn | Gly | Ala | Arg | Gly | Gln | Pro | Gly | Pro | Ala |
| | | | | 405 | | | | | 410 | | | | | 415 | |
| Pro | Pro | Ala | Asp | Glu | Glu | Ala | Gly | Pro | Pro | Pro | His | Leu | Val | His | Ala |
| | | | 420 | | | | | 425 | | | | | 430 | | |
| Phe | Gln | Gly | Ile | Asn | Lys | Leu | Leu | Gly | Thr | Thr | Pro | Ser | Asp | Ile | Asp |
| | | 435 | | | | | 440 | | | | | 445 | | | |
| Lys | Tyr | Ser | Arg | Ile | Val | Phe | Pro | Val | Cys | Cys | Val | Cys | Phe | Asn | Leu |
| | 450 | | | | | 455 | | | | | 460 | | | | |
| Met | Tyr | Trp | Ile | Ile | Tyr | Leu | His | Val | Ser | Asp | Val | Val | Ala | Asp | Asp |
| 465 | | | | | 470 | | | | | 475 | | | | | 480 |
| Leu | Val | Leu | Leu | Gly | Glu | Glu | Asn | | | | | | | | |
| | | | | 485 | | | | | | | | | | | |

( 2 ) INFORMATION FOR SEQ ID NO:5:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GGTCTAGAAC NACNGTNCTT ACNATGAAC 29

( 2 ) INFORMATION FOR SEQ ID NO:6:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GGCTCGAGGC RAANACCATN ACRARCCA 28

( 2 ) INFORMATION FOR SEQ ID NO:7:

( i ) SEQUENCE CHARACTERISTICS:
( A ) LENGTH: 128 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

TCTAGAACGA CGGTGGTTAC GATGACGACG CTCATGTCGT CCACGAATGC GGCTCTGCCC 60

-continued

AAGATCTCAT ATGTCAAGTC CATCGATGTC TATCTGGGAA CTTGTTTCGT CATGGTCTTC 120

GCCTCGAG 128

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

AGGTCCATCG ATGTCTATCT GGGAA 25

( 2 ) INFORMATION FOR SEQ ID NO:9:

( i ) SEQUENCE CHARACTERISTICS:
( A ) LENGTH: 279 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

AGGTCCATCG ATGTCTATCT GGGAACTTGT TTCGTCATGG TCTTCACCAG TTTACTAGAA 60

TATGCCACGG TTGGCTATAT GGCTAAAAGG ATACAGATGA GGAAACAAAG ATTCACTGCT 120

GTTCAAAAAA TGCAAATAGA TGGTCCTCCA GGGTCAGCTG AGCCTATCCC CCCACCGAGG 180

ACCAGCACCC TATCTAGGCC ACCACCTAGC CGATTATCGG AGGTTCGGTT CAAAGTTCAC 240

GATCCGAAGG CATATTCTAA AGGCGGTACT TTAGAAAAA 279

( 2 ) INFORMATION FOR SEQ ID NO:10:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

GTTCACGATC CGAAGGCATA TTCT 24

( 2 ) INFORMATION FOR SEQ ID NO:11:

( i ) SEQUENCE CHARACTERISTICS:
( A ) LENGTH: 575 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GTTCACGATC CGAAGGCATA TTCTAAAGGC GGTACTTTAG AAAACACTAT CAATGGGGCT 60

CGGGGCCAGC CAGGACCTGC TCCACCGGCA GACGAAGAAG CTGGACCACC TCCGCATCTC 120

GTTCATGCTT TCCAAGGTAT CAACAAACTG CTCGGCACGA CCCCCTCGGA CATCGACAAG 180

TACTCGCGCA TCGTGTTCCC CGTCTGCTTC GTTTGCTTTA ACCTTATGTA CTGGATCATT 240

TACCTTCACG TGTCTGACGT CGTGGCTGAT GACTTGGTAC TACTAGGCGA AGAAAATTGA 300

-continued

```
ATTCTCTTTA ACTATACCGG ACTTGTTTTA ACTATACCGG ACTTGTTTTA ACTTTAGGGT    360

GCTTATGATC AACCATCCAT CAAGTCTCGG TAAAGTTCTT TAAGTCTAGA ACGCTCAGTA    420

AAATAATAGC GTTCTTTGTG TTTATAAATA TAATTATAGT ACAGATCACT ATGTTTATTA    480

TAGATAAGTG TCGTGTATAT TGGCACTGGT AATATTAATT CTTTAGAAAA TAAAGATAAT    540

ATGAATTCAA AAAAAAAAAA AAAAAAAAAA AAAAA                               575
```

( 2 ) INFORMATION FOR SEQ ID NO:12:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

```
AACTTGCTCG AGACTTGATG GAT    23
```

LEPIDOPTERAN GABA GATED CHLORIDE CHANNEL AND NUCLEIC ACIDS ENCODING SUBUNITS THEREOF

FIELD OF THE INVENTION

The gamma-amino butyric acid (GABA) gated chloride channel is a primary target for insecticide action. The present invention provides isolated nucleic acids encoding a lepidopteran GABA gated chloride channel subunit useful for producing a recombinant lepidopteran GABA gated chloride channel. The recombinant GABA gated chloride channel provides a screening system for identifying agonists and antagonists useful as insecticides for lepidopteran pests including *Heliothis virescens.*

BACKGROUND OF THE INVENTION

GABA is the major inhibitory neurotransmitter in mammals and insects. In mammals, inhibition is mediated by two types of receptors. Mammalian $GABA_B$ receptors are coupled to calcium and potassium channels, while $GABA_A$ receptors form an integral chloride channel. Insect neuronal GABA receptors exhibit pharmacological similarity to mammalian $GABA_A$ receptors, but also exhibit critical differences, for example in the potency order for agonists and antagonists.

The insect GABA receptor is a primary target for insecticide action. Physiological and competitive binding studies indicate the presence of at least two insecticide-sensitive binding sites. Binding of insecticides to the noncompetitive blocker site acts to block the chloride channel of the GABA receptor, while binding of insecticides to the other site acts to activate the chloride channel. Insecticides that act to block the chloride channel include picrotoxinin (PTX) and the polychlorocycloalkanes (PCCAs).

Adverse toxicology has led to significant restrictions on the use of many insecticides, particularly PCCAs. Further, the selection of resistant pest strains has resulted in the ineffectiveness of some chloride channel blockers and activators as insecticides.

A better understanding of the insect GABA receptor is necessary to develop insecticides that are not subject to resistance, and that exhibit better selectivity and enhanced environmental safety.

Vertebrate GABA receptors from a number of sources have been cloned and functionally expressed. Olsen et al. (1990) *FASEB J.* 4: 1469. Cloning of the insect receptor has proven more difficult due to the lack of a suitable ligand for receptor purification. ffrench-Constant et al. (1991) *Proc. Natl. Acad. Sci.* 88: cloned a Drosophila GABA receptor by identifying a locus conferring PTX insensitivity linked to cyclodiene resistance. A single amino acid mutation was identified as responsible for insecticide resistance. ffrench-Constant et al. (1993) *Nature* 363: 449. Low stringency screening with the Drosophila probe was utilized to clone the cyclodiene resistance locus from another diptera, *Aedes aegypti.* Thompson et al. (1993) *FEBS Letters* 325: 187. To date, an insect GABA receptor has not been cloned from any other insect order.

Insects of the order lepidoptera are significant pests, and in particular the larvae are destructive defoliators. Further, lepidopteran pests are typically harder to control than diptera. Accordingly, there is a need to identify and develop safe and specific insecticides against lepidopteran pests. The present invention addresses this need by providing isolated nucleic acids encoding a lepidopteran GABA gated chloride channel subunit, recombinant lepidopteran GABA gated chloride channels, and a method of identifying lepidopteran GABA receptor agonists and antagonists.

SUMMARY OF THE INVENTION

The present invention is directed to an isolated nucleic acid encoding a lepidopteran GABA gated chloride channel subunit. In a preferred embodiment the nucleic acid is isolatable from *Heliothis virescens.* In another preferred embodiment the isolated nucleic acid has a sequence encoding the amino acid sequence of SEQ ID NO:2 or SEQ ID NO:4.

The present invention further provides expression vectors comprising a nucleic acid encoding a lepidopteran GABA gated chloride channel subunit. Host cells comprising the expression vectors are also provided.

Another aspect of the present invention provides a recombinant lepidopteran GABA gated chloride channel, and kits and compositions comprising a recombinant lepidopteran GABA gated chloride channel. A method for preparing a lepidopteran GABA gated chloride channel is also provided.

In yet another embodiment, the present invention provides a Xenopus oocyte comprising a nucleic acid encoding a lepidopteran GABA gated chloride channel subunit, and a Xenopus oocyte expressing a functional lepidopteran GABA gated chloride channel.

The present invention further provides a method of identifying agonists and antagonists to a lepidopteran GABA gated chloride channel.

DETAILED DESCRIPTION OF THE INVENTION

Figure 1:
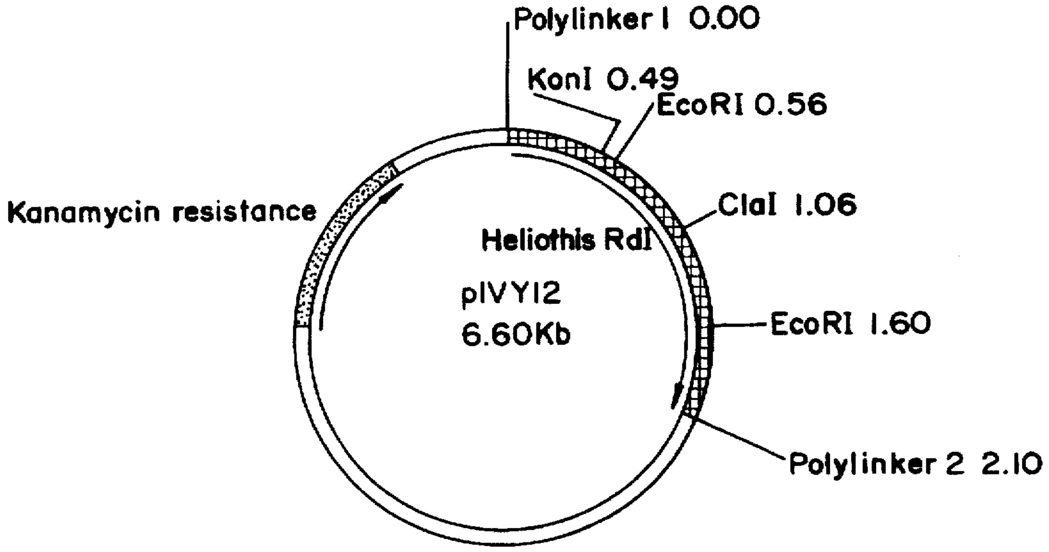
FIG. 1 depicts the plasmid pIVY12. The plasmid comprises the Heliothis sequence (SEQ ID NO:1) encoding the cyclodiene resistant GABA gated chloride channel subunit cloned into the EcoRI/XhoI sites of pBK-CMV (Stratagene).

The present invention is directed to isolated nucleic acids encoding lepidopteran GABA gated chloride channel subunits. An isolated nucleic acid encoding a lepidopteran GABA gated chloride channel subunit is defined herein as a nucleic acid isolatable from an insect of the order lepidoptera and capable of encoding, under appropriate conditions, a functional GABA gated chloride channel. In a preferred embodiment the nucleic acid is isolatable from Heliothis. In a more preferred embodiment the nucleic acid is isolatable from *Heliothis virescens.* A functional GABA gated chloride channel is defined herein as a protein or polypeptide multimer having the ability to bind GABA and thereby mediate chloride flux in a cell expressing the GABA gated chloride channel.

The isolated nucleic acid may be DNA or RNA, including cDNA and mRNA. In a preferred embodiment the isolated nucleic acid has a sequence encoding the amino acid sequence set forth in SEQ ID NO:2 or SEQ ID NO:4. The ordinarily skilled artisan, with the knowledge of the degeneracy of the genetic code, can determine DNA and RNA sequences that encode the amino acid sequence set forth in SEQ ID NO:2 or SEQ ID NO:4. Further, the sequence can be selected to optimize expression in a particular host organism by utilizing known preferred codons for the host organism of choice.

In another preferred embodiment, the isolated nucleic acid has the nucleotide sequence set forth in SEQ ID NO:1 or SEQ ID NO:3. In another embodiment, the isolated nucleic acid has the sequence of nucleotides 115 to 1581 of SEQ ID NO:1 or SEQ ID NO:3. Fragments of a nucleic acid having the sequence of SEQ ID NO:1 or SEQ ID NO:3 that maintain the ability to encode a functional lepidopteran GABA gated chloride channel are also encompassed by the present invention.

SEQ ID NO:1 contains the codon TCA at nucleotides 967–969 encoding the amino acid serine at amino acid position 285 in SEQ ID NO:2. SEQ ID NO:3 differs from SEQ ID NO:1 by the substitution of the codon GCA at nucleotides 967–969 encoding alanine at amino acid position 285 in SEQ ID NO:4. It has been discovered in accordance with the present invention that the nucleic acid having the sequence of SEQ ID NO:1 encodes a lepidopteran GABA gated chloride channel subunit and, when expressed in a host cell, provides a functional homomeric lepidopteran GABA gated chloride channel conferring cyclodiene resistance. The nucleic acid having the sequence of SEQ ID NO:3 encodes a lepidopteran GABA gated chloride channel subunit and, when expressed in a host cell, provides a functional homomeric lepidopteran GABA gated chloride channel that is less cyclodiene insensitive than the channel encoded by SEQ ID NO:1.

The present invention further encompasses nucleic acids isolatable from lepidoptera and capable of hybridizing under moderate or high stringency conditions to the complement of an isolated nucleic acid having the sequence of SEQ ID NO:1 or SEQ ID NO:3, and further capable of encoding, under appropriate conditions, a functional GABA gated chloride channel subunit. Moderate and high stringency hybridization conditions are known to the skilled artisan and described, for example, in Sambrook et al. (1989) *Molecular Cloning: A Laboratory Manual* Cold Spring Harbor Laboratory Press, Cold Spring Harbor, N.Y. Moderate stringency conditions, for example, are about 50° C., 2X SSC. The ability of the isolated nucleic acid of the present invention to encode a functional GABA gated chloride channel can be determined by functional assays as described hereinbelow.

The present invention is further directed to expression vectors comprising the isolated nucleic acids of the present invention. In the expression vectors of the present invention, the nucleic acid encoding a lepidopteran GABA gated chloride channel subunit is operably linked to suitable transcriptional and/or translational regulatory elements to effect expression of the GABA gated chloride channel receptor in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and vectors into which the nucleic acid of the invention can be inserted are also commercially available. Recombinant viral vectors, including retrovirus, baculovirus, parvovirus and densovirus vectors are particularly preferred.

In a preferred embodiment the expression vector comprises a strong constitutive or inducible promoter operably linked to a nucleic acid encoding a lepidopteran GABA gated chloride channel subunit. Suitable promoters are well known and readily available to one of ordinary skill in the art, and include for example, the polyhedrin promoter (Kitts et al., 1993, *BioTechniques,* 14:810), heat shock promoter (Stellar et al., 1985, *EMBO J.,* 4:167) and metallothionein promoter (Kaufman et al., 1989, *Cell* 59:359). Expression vectors can be constructed by well known molecular biological methods as described for example in Sambrook et al. (1989) *Molecular Cloning: A Laboratory Manual* Cold Spring Harbor Laboratory Press, Cold Spring Harbor, N.Y., or any of a myriad of laboratory manuals on recombinant DNA technology that are widely available. Expression vectors into which the nucleic acids of the present invention can be cloned under the control of a suitable promoter are also commercially available.

Another embodiment of the present invention provides host cells containing the expression vectors described above. The host cell may be procaryotic or eukaryotic, including bacterial, yeast, insect or mammalian. Insect and mammalian cells are preferred. Particularly preferred host cells include insect cell lines, including for example *Spodoptera frugiperda* and *Trichoplusia ni* cells. The host cells may be transformed, transfected or infected with the expression vectors of the present invention by methods well-known to one of ordinary skill in the art. Transfection may be accomplished by known methods, such as liposome mediated transfection, calcium phosphate mediated transfection, microinjection and electroporation. Permanently transformed insect cell lines are particularly preferred. For example, insect cell lines such as Drosophilia cell line SH1 can be transformed with the expression vectors of the present invention by commercially available lipofectin (GIBCO-BRL) to provide permanently transformed cell lines expressing a functional lepidopteran GABA gated chloride channel. In a preferred embodiment, the expression vector is designed such that expression of the chloride channel is inducible.

Expression systems utilizing baculovirus vectors and insect host cells are also preferred. The use of baculoviruses as recombinant expression vectors to infect lepidopteran insect cells is known in the art and described for example by Luckow et al. (1988) *Bio/Technology* 6: 47–55 and Miller (1988) *Ann. Rev. Microbiol.* 42:177–199. The baculovirus vectors generally contain a strong baculovirus promoter operably linked to a nucleic acid of the present invention such that the promoter directs expression of the lepidopteran GABA gated chloride channel. Baculovirus polyhedrin promoters such as the *Autographa californica* nuclear polyhedrosis virus polyhedrin promoter are preferred.

The baculovirus expression vectors of the present invention are made by inserting the nucleic acid encoding the lepidopteran GABA gated chloride channel subunit downstream of the polyhedrin promoter in a baculovirus transfer vector, for example pBacPac8 available from Clontech. Baculovirus transfer vectors further contain flanking baculovirus sequences that allow homologous recombination between the transfer vector and baculovirus DNA during co-transfection. The transfer vector containing the nucleic acid of the invention and viral DNA are used to co-transfect insect cells. In a preferred embodiment the insect cells are Spodoptera. *Spodoptera frugiperda* cells including Sf9 are particularly contemplated. During co-transfection, homologous recombination results in the transfer of an expression cassette containing the polyhedrin promoter and the nucleic acid of the present invention to the polyhedrin locus of the viral DNA. The resulting recombinant virus is used to generate viral stocks by standard methods. Insect host cells are infected with the recombinant virus to produce insect cells expressing the GABA gated chloride channel subunit.

The present invention further provides a Xenopus oocyte comprising a nucleic acid encoding a lepidopteran GABA gated chloride channel subunit, and a Xenopus oocyte expressing a functional lepidopteran GABA gated chloride channel. The Xenopus oocyte expression system is useful to identify nucleic acids capable of encoding functional lepidopteran GABA gated chloride channels. Xenopus oocytes expressing functional lepidopteran GABA gated chloride channels also provide a system for screening potential insecticides useful against insects of the order lepidoptera.

Xenopus oocytes comprising a nucleic acid encoding a lepidopteran GABA gated chloride channel subunit, and Xenopus oocytes expressing a functional lepidopteran GABA gated chloride channel can be made using the nucleic acids of the present invention and methods known to one of ordinary skill in the art. The use of Xenopus oocytes for the expression of exogenous nucleic acids coding for functional receptors is described, for example, by Barnard et al. (1982) *Proc. R. Soc. London B.* 215:241–246 and Fleming et al. (1991) *J. Physiol.* 438:371P. Expression vectors containing cDNA encoding the GABA gated chloride channel subunit under the control of a strong promoter can be injected into the nuclei of oocytes, after which oocytes are incubated for from one two several days, followed by assessment for presence of functional GABA gated chloride channels. Alternately, mRNA can be synthesized in vitro from cDNA encoding the GABA gated chloride channel subunit, and injected into oocytes, followed by assessment for presence of functional GABA gated chloride channels as described hereinbelow.

The present invention is further directed to recombinant lepidopteran GABA gated chloride channel. The recombinant lepidopteran GABA gated chloride channel may be isolated in a membrane preparation or present in the cell membrane of the host cell or oocyte in which it has been recombinantly produced. Whole cells and membrane preparations comprising the recombinant lepidopteran GABA gated chloride channel are particularly contemplated. Recombinant lepidopteran GABA gated chloride channel is useful, for example, to screen potential insecticides by specific binding assays or functional assays. The GABA gated chloride channel is defined herein as a protein or polypeptide or multimer thereof having the ability to bind GABA and thereby mediate chloride flux in a cell expressing the GABA gated chloride channel. The recombinant lepidopteran GABA gated chloride channel is the expression product of an isolated nucleic acid of the present invention.

In a preferred embodiment the nucleic acid is isolatable from Heliothis genus. In a more preferred embodiment the nucleic acid is isolatable from *Heliothis virescens*. In another preferred embodiment the isolated nucleic acid has a sequence encoding the amino acid sequence set forth in SEQ ID NO:2 or SEQ ID NO:4. The ordinarily skilled artisan, with the knowledge of the degeneracy of the genetic code, can determine DNA and RNA sequences that encode the amino acid sequence set forth in SEQ ID NO:2 and SEQ ID NO:4. Further, the sequence can be selected to optimize expression in a particular host organism by utilizing known preferred codons for the host organism of choice. In another preferred embodiment, the isolated nucleic acid has the nucleotide sequence set forth in SEQ ID NO:1 or SEQ ID NO:3. In another embodiment, the isolated nucleic acid has the sequence of nucleotides 115 to 1581 of SEQ ID NO:1 or SEQ ID NO:3. Fragments of a nucleic acid having the sequence of SEQ ID NO:1 or SEQ ID NO:3 that maintain the ability to encode a functional lepidopteran GABA gated chloride channel are also encompassed by the present invention. The present invention further encompasses nucleic acids isolatable from lepidoptera and capable of hybridizing under moderate or high stringency conditions to the complement of an isolated nucleic acid having the sequence of SEQ ID NO:1 or SEQ ID NO:3, and further capable of encoding, under appropriate conditions, a functional GABA gated chloride channel.

The present invention further provides a method of making a recombinant lepidopteran GABA gated chloride channel. It has been discovered in accordance with the present invention that expression of a nucleic acid encoding a lepidopteran GABA gated chloride channel subunit results in production of a functional homomeric GABA gated chloride channel. Recombinant lepidopteran GABA gated chloride channel is made by transforming, transfecting or infecting a suitable host cell with an expression vector comprising a nucleic acid encoding a lepidopteran GABA gated chloride channel subunit, culturing the host cell under conditions suitable for expression, and optionally recovering the recombinant lepidopteran GABA gated chloride channel. In a preferred embodiment, the recombinant lepidopteran GABA gated chloride channel is made in insect cells, preferably *Spodoptera frugiperda* 9, by infecting the insect cells with a recombinant virus in which the nucleic acid of the invention is under the control of a polyhedrin promoter, and culturing the cells under conditions suitable for expression of the recombinant lepidopteran GABA gated chloride channel. In another preferred embodiment, the recombinant lepidopteran GABA gated chloride channel is made in permanently transformed cell lines as described hereinabove.

A functional lepidopteran GABA gated chloride channel can be identified by one of ordinary skill in the art by functional or binding assays. An exhaustive review of techniques and protocols is provided in Rudy et al., eds. (1992) *Methods in Enzymology* 207, Academic Press, Inc., San Diego, Calif. For example, in a functional assay, whole cell voltage clamp recording of host cells or oocytes expressing the lepidopteran GABA gated chloride channel subunit can be used to assess chloride flux in response to application of GABA. Dose-dependent GABA-evoked currents indicate that a functional lepidopteran GABA gated chloride channel has been assembled. In a typical ligand-binding assay, potential agonists and antagonists are identified by their ability to displace radiolabeled ligands known to act as sites on the GABA receptor. Suitable ligands include GABA, muscimol, EBOB (n-propylethynylbicycloorthobenzoate), and TBPS (t-butylbicyclophosphorothionate), and BIDN (3,3-bis(trifluoromethyl)bicyclo[2.2.1]heptane-2,2-dicarbonitrile).

Another embodiment of the present invention provides a composition comprising a recombinant lepidopteran GABA gated chloride channel in a cell membrane. The composition may be a membrane preparation, including a freeze dried membrane preparation, or an intact cell or oocyte expressing the functional lepidopteran GABA gated chloride channel. The composition is useful, for example, to screen potential insecticides by functional or specific binding assays and may further comprise radiolabeled compounds. The composition may further comprise appropriate carriers or diluents, including, for example, physiological buffers.

The present invention further provides methods of identifying agonists and antagonists to a lepidopteran GABA gated chloride channel. Agonists to a lepidopteran GABA gated chloride channel are defined as compounds that, like GABA, when applied to the chloride channel result in opening of the channel as measured by flux of chloride ions into or out of the cell. Antagonists to a lepidopteran GABA gated chloride channel are defined as compounds that block the chloride channel, as measured for example by a decrease in GABA mediated chloride ion flux in the cell. A method of identifying an agonist comprises applying the putative agonist to a Xenopus oocyte, a cell or a membrane expressing the lepidopteran GABA gated chloride channel in the presence of chloride ions, and measuring chloride flux, wherein flux of chloride is indicative of an agonist. A method of identifying an antagonist comprises applying the putative antagonist to a Xenopus oocyte or a cell or membrane expressing the lepidopteran GABA gated chloride channel in the presence of chloride ions and measuring chloride flux, followed by applying the putative antagonist and GABA to the cell or membrane and measuring chloride flux; and comparing the chloride flux obtained in the presence of the putative antagonist and GABA to the flux obtained under similar conditions in the presence of GABA only, wherein a decrease in flux of chloride observed in the presence of the putative antagonist relative to the flux observed in the presence of GABA alone is indicative of an antagonist. In a preferred embodiment, chloride flux is measured by voltage clamp electrophysiology. In another preferred embodiment, the cell is an recombinant baculovirus-infected Sf9 cell or a permanently transformed cell line. In another preferred embodiment, the concentrations of agonists, antagonists and GABA are from about 0.1 nM to about 1.0 mM.

Agonists and antagonists against the lepidopteran GABA gated chloride channel can also be identified by ligand binding assays. Agonists and antagonists are identified by their ability to displace radiolabeled ligands known to act as agonists or antagonists, respectively. The recombinant GABA gated chloride channel, present in an oocyte, cell, or membrane, (preferably a membrane) is incubated with radiolabeled ligand and unlabeled candidate agonist or antagonist. After incubation, the incubation mixture is filtered, and radioactivity retained on the filters is measured by methods known in the art, for example liquid scintillation counting. The ability of the candidate compound to inhibit specific binding of the radiolabeled ligand provides a measure of the compound's agonist or antagonist activity.

Agonists and antagonists against the lepidopteran GABA gated chloride channel are useful as insecticides against lepidoptera. It has been discovered in accordance with the present invention that the lepidopteran GABA gated chloride channel exhibits distinct pharmacology relative to GABA gated chloride channels of mammals and other insects. Thus, the present recombinant lepidopteran GABA gated chloride channel allows identification of lepidopteran-specific insecticides heretofore not possible even with other insect channels. Lepidopteran pests are typically harder to control than diptera, perhaps because Lepidoptera feed on alkaloid-containing plant tissue, such as cotton. Thus lepidopteran pest control is unique, as reflected by the distinct pharmacology of the lepidopteran GABA gated chloride channel described herein. Accordingly, the present invention solves a need in the art by providing methods of identifying insecticides against lepidoptera.

It has further been discovered that the functional assays described hereinabove for identification of agonists and antagonists are particularly well-correlated with data from whole insect screening. For example, the level of activity as measured by $IC_{50}$ for fipronil in oocytes expressing the lepidopteran GABA gated chloride channel is predictive of the activity of fipronil on whole insects as measured by $LD_{50}$. Further, the effect of fipronil in electrophysiological studies of oocytes expressing the lepidopteran GABA gated chloride channel is correlated with fipronil activity in Heliothis larvae. Thus the discovery of the lepidopteran GABA gated chloride channel and the methods described herein allows the identification of insecticide compounds that are uniquely suited to targeting of lepidopteran pests.

The present invention further provides a kit for identifying agonists and antagonists to a lepidopteran GABA gated chloride channel. The kit contains a first container containing a recombinant lepidopteran GABA receptor in a cell membrane. The membrane may be in the form of a membrane preparation, including a freeze dried membrane preparation, or an intact cell or oocyte expressing the functional lepidopteran GABA gated chloride channel. The kit of the present invention optionally further comprises radiolabeled binding ligands known to act at sites on the GABA gated chloride channel. In a preferred embodiment, the ligand is radiolabeled GABA, muscinol, EBOB, TBPS and BIDN. The compositions and kits of the present invention are useful for identifying lepidopteran insecticides by functional assays, binding assays, immunoassays, scintillation proximity assays, and biomolecular interaction analysis using surface plasmon resonance, for example as described by Malmquist et al. (1994) *Methods: A Companion to Methods in Enzymology* 6:95.

The following examples further illustrate the present invention.

EXAMPLE I

Isolation of a Full Length cDNA Encoding Cyclodiene Resistant GABA Gated Chloride Channel Subunit Genomic DNA was obtained from a Rhone Poulenc in-house population of *Heliothis virescens* obtained from a field strain by the modified CTAB (cetyltrimethylammonium bromide) method described by Rogers et al. (1985) *Plant Mol. Biol.* 5:69. The genomic DNA was amplified by polymerase chain reaction (PCR) using degenerate primers vw121403 and vw123002 and Amplitaq polymerase (Perkin Elmer following the manufacturer's instructions. Primer vw121403 has the sequence 5'-GGT CTA GAA CIA CIG TIC TTA CIA TGA AC-3' (SEQ ID NO:5). Primer vw123002 has the sequence 5'-GGC TCG AGG C(A/G)A AIA CCA TIA C(A/G)A (A/G)CC A-3' (SEQ ID NO:6).

PCR resulted in the amplification of a 70 base pair (bp) fragment which was cloned into the pKS+ plasmid (Stratagene) to produce pJW1 and sequenced. The amplified fragment had the following sequence: 5'-TCT AGA ACG ACG GTG GTT ACG ATG ACG ACG CTC ATG TCG TCC ACG AAT GCG GCT CTG CCC AAG ATC TCA TAT GTC AAG TCC ATC GAT GTC TAT CTG GGA ACT TGT TTC GTC ATG GTC TTC GCC TCG AG-3' (SEQ ID NO:7).

The technique of rapid amplification of cDNA ends (RACE) according to Frohman et al. (1988) *Proc. Natl. Acad. Sci. USA* 85:8998 was used to obtain the 3' end of the *Heliothis virescens* mRNA. PolyA mRNA was isolated from a mixed population of developing *Heliothis virescens* embryos obtained from a Rhone Poulenc in-house population. One microgram of polyA mRNA was used with a 3'RACE kit (GIBCO-BRL) following the manufacturer's instructions and utilizing as the specific primer vw052802, derived from the 70 bp fragment and having the sequence 5'-AGG TCC ATC GAT GTC TAT CTG GGA A-3' (SEQ ID NO:8). The amplified fragment from the first 3'RACE was cloned into the plasmid pKS+ to produce a plasmid designated pIVY7. Sequencing indicated that the fragment had the sequence: 5'-AGG TCC ATC GAT GTC TAT CTG GGA ACT TGT TTC GTC ATG GTC TTC ACC AGT TTA CTA GAA TAT GCC ACG GTT GGC TAT ATG GCT AAA AGG ATA CAG ATG AGG AAA CAA AGA TTC ACT GCT GTT CAA AAA ATG CAA ATA GAT GGT CCT CCA GGG TCA GCT GAG CCT ATC CCC CCA CCG AGG ACC AGC ACC CTA TCT AGG CCA CCA CCT AGC CGA TTA TCG GAG GTT CGG TTC AAA GTT CAC GAT CCG AAG GCA TAT TCT AAA GGC GGT ACT TTA GAA AAA-3' (SEQ ID NO:9).

Because the anchor primer had annealed to an A-rich region in the *Heliothis virescens* coding region, a second 3'RACE was performed utilizing as the specific primer vw112293-301, derived from the amplified fragment of the first 3'RACE and having the sequence 5'-GTT CAC GAT CCG AAG GCA TAT TCT-3' (SEQ ID NO:10). The amplified product was cloned into pKS+ to generate plasmid pIVY10. Sequencing indicated that the amplified product had the sequence: GTT CAC GAT CCG AAG GCA TAT TCT AAA GGC GGT ACT TTA GAA AAC ACT ATC AAT GGG GCT CGG GGC CAG CCA GGA CCT GCT CCA CCG GCA GAC GAA GAA GCT GGA CCA CCT CCG CAT CTC GTT CAT GCT TTC CAA GGT ATC AAC AAA CTG CTC GGC ACG ACC CCC TCG GAC ATC GAC AAG TAC TCG CGC ATC GTG TTC CCC GTC TGC TTC GTT TGC TTT AAC CTT ATG TAC TGG ATC ATT TAC CTT CAC GTG TCT GAC GTC GTG GCT GAT GAC TTG GTA CTA CTA GGC GAA GAA AAT TGA ATTCTCTT-TAACTATACCGGACTTGTTTTAAC-TATACCGGACTTGTTTTAACTTTA GGGTGCTTAT-GATCAACCATCCATCAAGTCTCGGTAAAGTTCTTTA AGTCTAGAAC GCTCAGTAAAATAATAGCGT-TCTTTGTGTTTATAAATATAATTATAGTACAGATCA CTATGTTTATTATAGATAAGTGTCGTG-TATATTGGCACTGGTAATATTAATTCTTT AGAAAATAAAGATAATATGAATTCAAAAAAAAAAA AAAAAAAAAAAAAAAA-3' (SEQ ID NO:11). Nucleotides in groups of three represent coding sequences and the unbroken nucleotide sequence represents non-translated mRNA sequence. The non-translated sequence ends with 27 consecutive A residues and is downstream from a translation stop codon.

A specific primer designated vw040401 was synthesized based upon the non-translated 3' end of the *Heliothis virescens* mRNA identified by 3'RACE. Primer vw040401 has the sequence 5'-AACTTGCTCGAGACTTGATGGAT-3' (SEQ ID NO:12) and was used to construct a *Heliothis virescens* cDNA library. Five micrograms of polyA mRNA isolated from a mixed *Heliothis virescens* embryo population was used to make the library. Primer vw040401 was engineered to contain an XhoI site and was then substituted for the first strand primer in the Zap cDNA synthesis kit (Stratagene). The cDNA was made according to the manufacturer's instructions and then cloned into the lambda ZAP expression vector cloning system (Stratagene) and packaged with Gigapack II packaging system (Stratagene) following the manufacturer's instructions. Thus a non-amplified library of $5\times10^5$ recombinants was made and then amplified.

Part of the amplified library was screened with $^{32}P$ labeled random primer derived probes of the 3'RACE inserts of plasmids pIVY7 and pIVY10 using standard techniques. One positive clone was identified and plaque purified. The phagemid pBK-CMV containing the insert was excised following the manufacturer's instructions (Stratagene). The 6.6 kb phagemid clone, designated pIVY12, consists of the Heliothis sequence cloned into the EcoRI/XhoI sites of pBK-CMV and is depicted in FIG. 1. Polylinker 1 at position 0.0 contains recognition sites for SacI, BssHI, PstI, SPEI, BamHI and EcoRI. Polylinker 2 at position 2.10 contains recognition sites for XhoI, ScaI, XbaI, NotI, ApaI, ClaI, BstXI, SmaI and KpnI. Double stranded sequencing was accomplished with the Sequenase system (Amersham). The following DNA sequence (SEQ ID NO:1) was determined.

```
        10        20        30        40        50
GAATTCGGCACGAGGACGCCTGAGGGCCTGTAAGAACACGCCAGTCCGGC

        60        70        80        90       100
CGGCACGGTGATACGCGGCTGCCGGCAGCCAGCGTCCGCAAGGGCGCACG

       110       120       130       140       150
CGGACCTGCAAAACATGCATACGAGCCGTCCGCGCGGCGTGCACAGCATC

       160       170       180       190       200
GCGCTAGTGCTGTCTCTCGCGATTGCCTGGTTACCTCATGCTGACCATGC

       210       220       230       240       250
CGCGGGAGCGGGAGGAGGGGGAATGTTTGGTGACGTCAATATCTCAGCCA

       260       270       280       290       300
TTTTGGATTCGCTAAGTGTAAGCTACGACAAAAGAGTGAGGCCGAACTAT

       310       320       330       340       350
GGAGGACCGCCAGTGGATGTGGGAGTCAACATGTACGTGCTCTCCATCAG
```

-continued

```
         360         370         380         390         400
CTCCTTATCTGAAGTGAAAATGGATTTCACCCTGGATTTCTACTTCAGAC

         410         420         430         440         450
AATTTTGGACAGACCCCAGGCTTGCTTACAAAAAAAGCACGGGTGTGGAG

         460         470         480         490         500
ACTCTGTCCGTCGGCTCGGAATTTATTAGAAACATATGGGTACCCGACAC

         510         520         530         540         550
CTTCTTTGTTAACGAAAAACAGTCATATTTCCACATAGCTACTACAAGCA

         560         570         580         590         600
ACGAATTCATACGCATTCATCATTCTGGATCTATTACTAGGAGTATAAGA

         610         620         630         640         650
CTGACTATCACCGCTTCTTGTCCGATGGATTTGCAGTATTTTCCGATGGA

         660         670         680         690         700
CCGTCAATTATGCAATATTGAAATCGAAAGTTTTGGCTACACCATGCGGG

         710         720         730         740         750
ACATCCGATACAAGTGGAATGAGGGGCCCAACTCAGTGGGTGTGTCGAGC

         760         770         780         790         800
GAAGTGTCTTTGCCGCAATTCAAGGTGCTGGGCCACCGGCAGCGGGCCAT

         810         820         830         840         850
GGAGATTTCTCTTACGACAGGAAACTACTCTCGTCTGGCATGTGAAATTC

         860         870         880         890         900
AATTTGTAGGCTCGATGGGATACTATTTAATTCAGATTTATATTCCGTCT

         910         920         930         940         950
GGCCTAATTGTCATTATATCTTGGGTATCATTTTGGTTGAATCGAAATGC

         960         970         980         990        1000
GACACCTGCAAGGGTATCACTAGGTGTCACAACTGTATTGACGATGACGA

        1010        1020        1030        1040        1050
CGCTCATGTCGTCCACGAATGCGGCTCTGCCCAAGATCTCATATGTCAAG

        1060        1070        1080        1090        1100
TCCATCGATGTCTATCTGGGAACTTGTTTCGTCATGGTCTTCACCAGTTT

        1110        1120        1130        1140        1150
ACTAGAATATGCCACGGTTGGCTATATGGCGAAAAGGATACAGATGAGGA

        1160        1170        1180        1190        1200
AACAAAGATTCACTGCTGTTCAAAAAATGCAAATAGATGGTCCTCCAGGG

        1210        1220        1230        1240        1250
TCAGCTGAGCCTATCCCCCCACCGAGGACCAGCACCCTATCTAGGCCACC

        1260        1270        1280        1290        1300
ACCTAGCCGATTATCGGAGGTTCGGTTCAAAGTTCACGATCCGAAGGCAT

        1310        1320        1330        1340        1350
ATTCTAAAGGCGGTACTTTAGAAAACACTATCAATGGGGCTCGGGGCCAG

        1360        1370        1380        1390        1400
CCAGGACCTGCTCCACCGGCAGACGAAGAAGCTGGACCACCTCCGCATCT

        1410        1420        1430        1440        1450
CGTTCATGCTTTCCAAGGTATCAACAAACTGCTCGGCACGACCCCCTCGG

        1460        1470        1480        1490        1500
ACATCGACAAGTACTCGCGCATCGTGTTCCCCGTCTGCTGCGTTTGCTTT

        1510        1520        1530        1540        1550
AACCTTATGTACTGGATCATTTACCTTCACGTGTCTGACGTCGTGGCTGA

        1560        1570        1580        1590        1600
TGACTTGGTACTACTAGGCGAAGAAAATTGAATTCTCTTTAACTATACCG

        1610        1620        1630        1640        1650
GACTTGTTTTAACTTAGGGTGCTTATGATCAACCATCCATCAGGTTTCGG

   1657
TAAAGTT
```

Sequencing indicated that pIVY12 encoded a full length *Heliothis virescens* Rdl clone directionally cloned into the EcoRI and XhoI sites of phagemid pBK-CMV. The coding sequence starts at 115 bp and ends at 1581 bp, and encodes a polypeptide of 488 amino acids having the predicted sequence: MHTSRPRGVHSIALVLSLAIAWL-
PHADHAAGAGGGGMFGDVNISAILDSLSVSYDK
RVRPNYGGPPVDVGVNMYVL-
SISSLSEVKMDFTLDFYFRQFWTDPRLAYKKSTGVE
TLSVGSEFIRNIWVPDTFFVNEKQSYF-
HIATTSNEFIRIHHSGSITRSIRLTITAS CPMDLQYFPM-
DRQLCNIEIESFGYTMRDIRYKWNEGP-
NSVGVSSEVSLPQFKVLGH
RQRAMEISLTTGNYSRLA-
CEIQFVGSMGYYLIQIYIPSGLIVIISWVSFWLNRNAT
PARVSLGVTTVLTMTTLMSSTNAALPKI-
SYVKSIDVYLGTCFVMVFTSLLEYATVG
YMAKRIQMRKQRFTAVQKMQIDGPPG-
SAEPIPPPRTSTLSRPPPSRLSEVRFKVHD PKAYSKG-
GTLENTINGARGQPGPAPPADEEAGPP-
PHLVHAFQGINKLLGTTPSDID

KYSRIVFPVCCVCFNLMYWIIYLHVSDV-
VADDLVLLGEEN (SEQ ID NO:2).

EXAMPLE II

Site-Directed Mutagenesis of cDNA Encoding Cyclodiene Resistant GABA Gated Chloride Channel Subunit The serine residue encoded by nucleotides TCA at positions 967–969 in plasmid pIVY12 was mutated to alanine (encoded by nucleotides GCA) by site-directed mutagenesis by overlap extension using the polymerase chain reaction as described by Ho et al. (1989) *Gene* 77: 51–59 using the Pfu polymerase (Stratagene). The mutation was verified by DNA sequence analysis from a number of full length clones. The cDNA insert of a representative plasmid, pIVY16, has the following sequence (SEQ ID NO:3):

```
        10         20         30         40         50
GAATTCGGCACGAGGACGCCTGAGGGCCTGTAAGAACACGCCAGTCCGGC

        60         70         80         90        100
CGGCACGGTGATACGCGGCTGCCGGCAGCCAGCGTCCGCAAGGGCGCACG

       110        120        130        140        150
CGGACCTGCAAAACATGCATACGAGCCGTCCGCGCGGCGTGCACAGCATC

       160        170        180        190        200
GCGCTAGTGCTGTCTCTCGCGATTGCCTGGTTACCTCATGCTGACCATGC

       210        220        230        240        250
CGCGGGAGCGGGAGGAGGGGGAATGTTTGGTGACGTCAATATCTCAGCCA

       260        270        280        290        300
TTTTGGATTCGCTAAGTGTAAGCTACGACAAAAGAGTGAGGCCGAACTAT

       310        320        330        340        350
GGAGGACCGCCAGTGGATGTGGGAGTCAACATGTACGTGCTCTCCATCAG

       360        370        380        390        400
CTCCTTATCTGAAGTGAAAATGGATTTCACCCTGGATTTCTACTTCAGAC

       410        420        430        440        450
AATTTTGGACAGACCCCAGGCTTGCTTACAAAAAAAGCACGGGTGTGGAG

       460        470        480        490        500
ACTCTGTCCGTCGGCTCGGAATTTATTAGAAACATATGGGTACCCGACAC

       510        520        530        540        550
CTTCTTTGTTAACGAAAAACAGTCATATTTCCACATAGCTACTACAAGCA

       560        570        580        590        600
ACGAATTCATACGCATTCATCATTCTGGATCTATTACTAGGAGTATAAGA

       610        620        630        640        650
CTGACTATCACCGCTTCTTGTCCGATGGATTTGCAGTATTTTCCGATGGA

       660        670        680        690        700
CCGTCAATTATGCAATATTGAAATCGAAAGTTTTGGCTACACCATGCGGG

       710        720        730        740        750
ACATCCGATACAAGTGGAATGAGGGGCCCAACTCAGTGGGTGTGTCGAGC

       760        770        780        790        800
GAAGTGTCTTTGCCGCAATTCAAGGTGCTGGGCCACCGGCAGCGGGCCAT

       810        820        830        840        850
GGAGATTTCTCTTACGACAGGAAACTACTCTCGTCTGGCATGTGAAATTC

       860        870        880        890        900
AATTTGTAGGCTCGATGGGATACTATTTAATTCAGATTTATATTCCGTCT

       910        920        930        940        950
GGCCTAATTGTCATTATATCTTGGGTATCATTTTGGTTGAATCGAAATGC

       960        970        980        990       1000
GACACCTGCAAGGGTAGCACTAGGTGTCACAACTGTATTGACGATGACGA
```

-continued

```
        1010        1020        1030        1040        1050
CGCTCATGTCGTCCACGAATGCGGCTCTGCCCAAGATCTCATATGTCAAG

        1060        1070        1080        1090        1100
TCCATCGATGTCTATCTGGGAACTTGTTTCGTCATGGTCTTCACCAGTTT

        1110        1120        1130        1140        1150
ACTAGAATATGCCACGGTTGGCTATATGGCGAAAAGGATACAGATGAGGA

        1160        1170        1180        1190        1200
AACAAAGATTCACTGCTGTTCAAAAAATGCAAATAGATGGTCCTCCAGGG

        1210        1220        1230        1240        1250
TCAGCTGAGCCTATCCCCCCACCGAGGACCAGCACCCTATCTAGGCCACC

        1260        1270        1280        1290        1300
ACCTAGCCGATTATCGGAGGTTCGGTTCAAAGTTCACGATCCGAAGGCAT

        1310        1320        1330        1340        1350
ATTCTAAAGGCGGTACTTTAGAAAACACTATCAATGGGGCTCGGGGCCAG

        1360        1370        1380        1390        1400
CCAGGACCTGCTCCACCGGCAGACGAAGAAGCTGGACCACCTCCGCATCT

        1410        1420        1430        1440        1450
CGTTCATGCTTTCCAAGGTATCAACAAACTGCTCGGCACGACCCCCTCGG

        1460        1470        1480        1490        1500
ACATCGACAAGTACTCGCGCATCGTGTTCCCCGTCTGCTGCGTTTGCTTT

        1510        1520        1530        1540        1550
AACCTTATGTACTGGATCATTTACCTTCACGTGTCTGACGTCGTGGCTGA

        1560        1570        1580        1590        1600
TGACTTGGTACTACTAGGCGAAGAAAATTGAATTCTCTTTAACTATACCG

        1610        1620        1630        1640        1650
GACTTGTTTTAACTTAGGGTGCTTATGATCAACCATCCATCAGGTTTCGG

    1657
TAAAGTT
```

The coding sequence starts at 115 bp and ends at 1581 bp, and encodes a polypeptide of 488 amino acids having the predicted sequence: MHTSRPRGVHSIALVLSLAIAWL-PHADHAAGAGGGGMFGDVNISAILDSLSVSYDKRVRPNYGGPPVDVGVNMYVL-SISSLSEVKMDFTLDFYFRQFWTDPRLAYKKSTGVETLSVGSEFIRNIWVPDTFFVNEKQSYF-HIATTSNEFIRIHHSGSITRSIRLTITAS CPMDLQYFPM-DRQLCNIEIESFGYTMRDIRYKWNEGP-NSVGVSSEVSLPQFKVLGHRQRAMEISLTTGNYSRLA-CEIQFVGSMGYYLIQIYIPSGLIVIISWVSFWLNRNATPARVALGVTTVLTMTTLMSSTNAALPKI-SYVKSIDVYLGTCFVMVFTSLLEYATVGYMAKRIQMRKQRFTAVQKMQIDGPPG-SAEPIPPPRTSTLSRPPPSRLSEVRFKVHD PKAYSKG-GTLENTINGARGQPGPAPPADEEAGPP-PHLVHAFQGINKLLGTTPSDIDKYSRIVFPVCCVCFNLMYWIIYLHVSDV-VADDLVLLGEEN (SEQ ID NO:2). In vitro transcribed mRNA was made from the mutated cDNA encoded by plasmid pIVY16 and used for oocyte physiological studies.

EXAMPLE III

Figure 2:
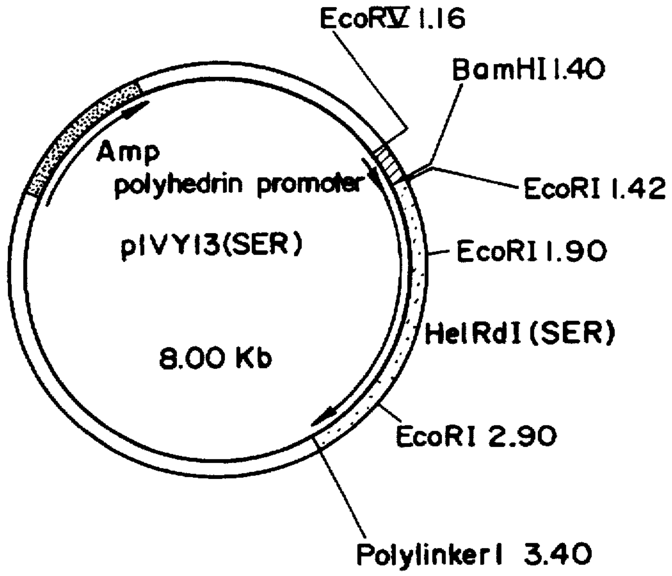
FIG. 2 depicts the plasmid pIVY13. The plasmid comprises a BamHI/XhoI fragment of PIVY12 cloned into the baculovirus transfer vector pBacPac8.

Expression of cDNA Encoding Cyclodiene Resistant GABA Gated Chloride Channel Subunit in Baculovirus Expression System A BamHI/XhoI DNA fragment from plasmid pIVY12 described in Example 1 containing the complete coding sequence of the *Heliothis virescens* cyclodiene resistant GABA gated chloride channel subunit was cloned into the baculovirus transfer vector pBacPac8 (Clontech). The resulting vector, pIVY13, contains cDNA encoding the *Heliothis virescens* cyclodiene resistant GABA gated chloride channel subunit under the control of the polyhedrin promoter. The 8.0 kb vector, PIVY13, consists of the Heliothis sequence of pIVY12 cloned into the BamHI/XhoI site of pBacPac8 and is depicted in FIG. 2. *Spodoptera frugiperda* 9 (Sf9) cells were cotransfected by pIVY13 and wild type *Autographa californica* nuclear polyhedrosis virus (AcMNPV) using the lipofectin procedure. In transfer vector pIVY13, flanking AcMNPV sequences allowed recombination with the viral DNA, thus resulting in the transfer of the expression cassette of the Heliothis cDNA and the polyhedrin promoter to the polyhedrin locus of the viral DNA. The recombinant virus thus generated was designated Elise13. Viral stocks of Elise13 were generated by standard procedures described by O'Reilly et al. (1992) *Baculovirus Expression Vectors, A Laboratory Manual*, W. H. Freeman and Company. Sf9 cells were infected with Elise13 at a multiplicity of infection of 5 plaque forming units (PFU) per cell by standard procedures.

Figure 3:
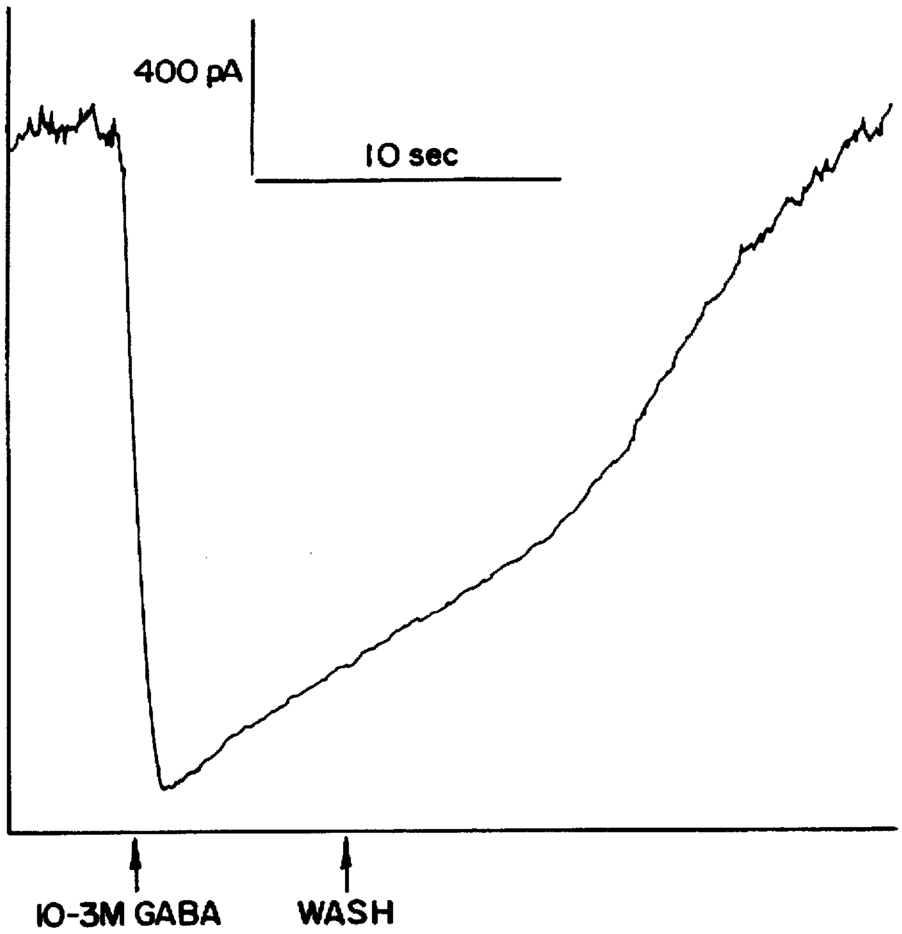
FIG. 3 presents the results of whole cell voltage clamp recordings made 30 hours after infection of Sf9 cells with a baculovirus vector containing cDNA encoding a lepidopteran GABA gated chloride channel.

To verify that expression of cDNA encoding the GABA gated chloride channel subunit results in production of a functional GABA gated chloride channel, hole cell voltage clamp recordings were made at thirty hours post infection. Results of the whole cell voltage clamp recordings are presented in FIG. 3. Application of $1\times10^{-3}$M GABA is indicated by the arrow marked "on." The data in FIG. 3 indicate that GABA exhibits the gross functional effect on the GABA gated chloride channel, i.e. flux of chloride ion. The results presented in this example indicate that expression of DNA encoding a lepidopteran GABA gated chloride channel subunit in Sf9 cells results in a functional GABA gated chloride channel.

EXAMPLE IV

Expression of Nucleic Acid Encoding Lepidopteran GABA Gated Chloride Channel in Xenopus Oocytes Messenger RNA was produced from the cDNA template of pIVY12 described in Example I by in vitro transcription with the Ambion mMESSAGE mMACHINE IN VITRO TRANSCRIPTION KIT™ (Ambion, Inc.) The mRNA was injected into oocytes by the following procedure.

Frogs were anesthetized in a 2 gram/liter solution of 3-amino benzoic acid ethyl ester for thirty minutes, after which oocytes were surgically removed from the abdominal cavity. Follicles were digested by collagenase treatment under sterile conditions by standard methods. Oocytes were injected with 50 nl of mRNA by glass electrodes.

Figure 4:
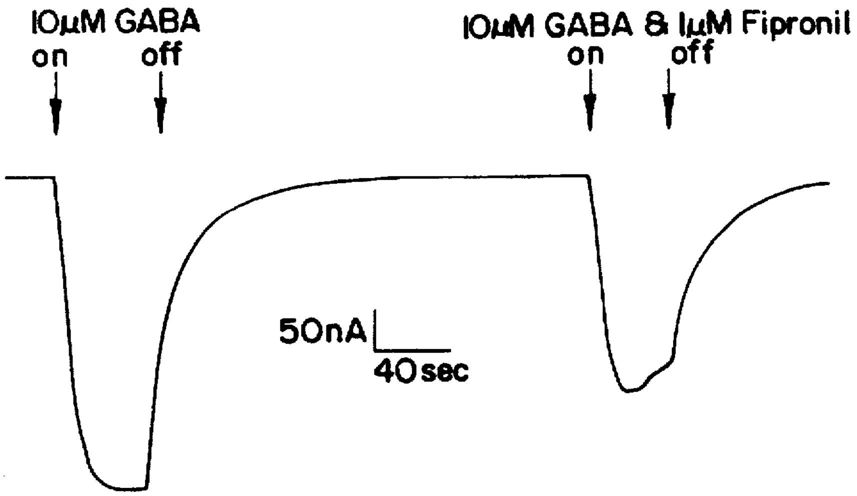
FIG. 4 presents electrophysiological recordings demonstrating the effect of GABA and fipronil on a lepidopteran GABA gated chloride channel expressed in oocytes.

Following a 24 to 48 hour incubation, two-electrode voltage clamp recordings were made. Recordings were made using a Dagan TEV200 voltage clamp interfaced with a MacLab4 data acquisition system running the MacLab Chart data acquisition/analysis software. Oocytes were positioned under a dissecting scope under constant perfusion with ND-96 standard saline using a Razel syringe perfusion pump, model A99-FY at 93.9 cc/hr. Glass electrodes (A-M Systems, Inc., 1.5 mm×0.86 mm) were filled with 3M KCl and resistance (a function of the diameter of the channel opening) was measured to be between 0.7 and 1.5 mega ohms. Both electrodes were inserted into the oocyte at opposite sides, the resting potential was recorded and the voltage clamp turned on. Oocytes were held at a resting potential between −70 and −50 mV. Control responses of GABA were obtained by stopping the perfusion of saline and perfusing with a known concentration of GABA in ND-96 with 0.1% DMSO. The average of several GABA applications was taken as the maximal chloride current for that particular GABA dose. The effect of 10 micromolar GABA on the lepidopteran GABA gated chloride channel expressed in Xenopus oocytes is depicted in FIG. 4. GABA application is indicated by the arrow marked "on." The data in FIG. 4 indicate that GABA exhibits the predicted gross functional effect on the GABA gated chloride channel. Further evidence that expression of the GABA gated chloride channel subunit in oocytes results in a functional GABA gated chloride channel was provided by similar assays with muscimol, a known GABA agonist, and picrotoxinin, a known GABA antagonist, both of which exhibited the predicted gross effects. Although known agonists and antagonists exhibited the predicted gross effects, the discrete pharmacology of the lepidopteran GABA gated chloride channel was determined to be unique, particularly with regard to chloride channel blockers (antagonists). In particular, the channels consistently exhibited a decreased sensitivity to the block of chloride ion efflux by inhibitors such as picrotoxinin and fipronil, when agonized by GABA, as shown in FIG. 4. In particular, the *Heliothis virescens* cyclodiene resistant chloride channel is about ten times less sensitive to block by fipronil than the Drosophila Rdl chloride channel. Sensitivity to picrotoxinin is also reduced by more than 100 times relative to Drosophila Rdl. In particular, 10 micromoles of picrotoxinin will result in nearly complete block of Drosophila Rdl (ffrench-Constant et al., 1993, *Nature* 363: 449–451), while the same dose applied to the Heliothis channel will result in about a fifty percent block. This example demonstrates that the expression of mRNA corresponding to the cDNA in pIVY12 results in a functional GABA gated chloride channel in oocytes, and further that the channel exhibits gross pharmacology similar to other chloride channels, but discrete pharmacology that distinguishes it from other characterized insect chloride channels.

EXAMPLE V

Figure 5:
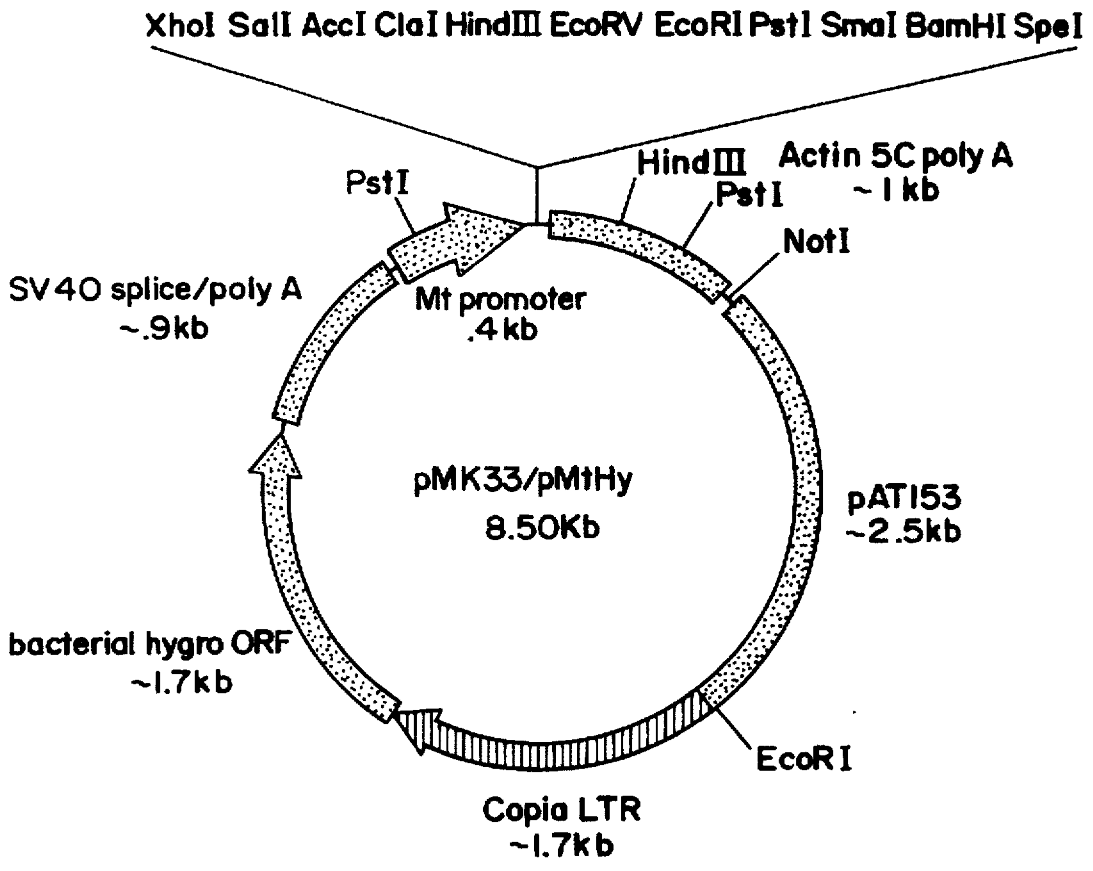
FIG. 5 depicts the plasmid pMK33. The vector is capable of expressing proteins under the control of the Drosophila metallothionein (Mt) promoter, and also carries a hygromycin resistance gene.

Production of Permanently Transformed Cell Lines Expressing a Functional GABA Gated Chloride Channel Plasmid pIVY17 was constructed by digesting pIVY12 with XbaI and BamHI, releasing a 2.2 kbp DNA fragment containing the coding region of the Heliothis Rdl cDNA. The 2.2 kbp fragment was cloned into the SpeI and BamHI sites of pMK33. Plasmid pMK33 is depicted in FIG. 5 and was obtained form David S. Hogness, Departments of Biochemistry and Developmental Biology, Stanford University Medical Center, Stanford, Calif. The expression vector pMK33 is designed to express proteins under the control of the Drosophila metallothionein (Mt) promoter, and also carries a hygromycin resistance gene, allowing selection of stable cell lines carrying the plasmid.

Figure 6:
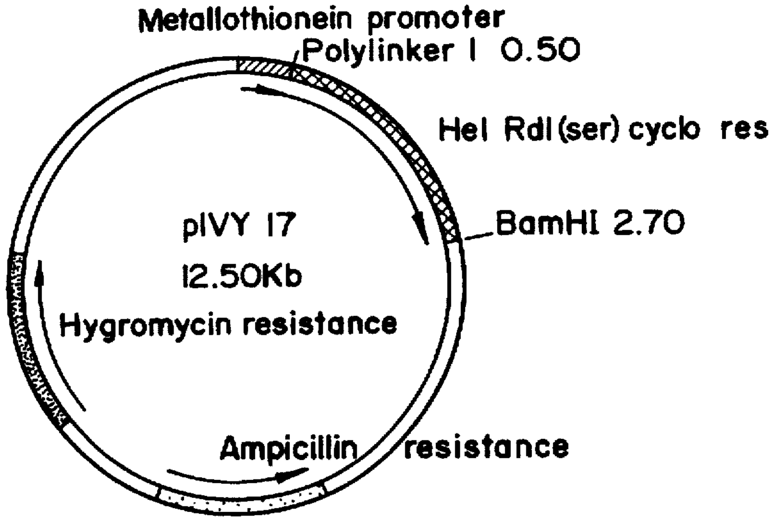
FIG. 6 depicts the plasmid pIVY17. The plasmid comprises the Heliothis sequence encoding the GABA gated chloride channel subunit under the control of the metallothionein promoter.

The resulting plasmid pIVY17 contains the Heliothis Rdl cDNA under the control of the metallothionein promoter. The 12.50 kb plasmid pIVY17 is depicted in FIG. 6.

The 8.0 kb plasmid pMK33, also designated pMtHy, can also be obtained by inserting the EcoRI-NotI fragment of pHSX-MT (Kaufman et al., *Cell* 59:359–371, 1989), containing the Drosophila Mt promoter, into BamHI-, NotI-cleaved pcophyg (Rio et al., *Cell* 44:21–32, 1986) filling in the EcoRI and BamHI ends. The 3' end of the Actin 5C gene is then inserted into pMT/HyI in two steps. The SalI fragment of pPac (Krasnow et al., *Cell* 57:1031–1043, 1989) containing the actin 5C 3' end, is first cloned into the Bluescript+KS (Stratagene) XbaI site, filling in the ends. The XhoI-NotI fragment of the resulting plasmid is then inserted into XhoI-, NotI-cleaved pMt/HyI, to create pMt/Hy. XhoI, EcoRV, BamHI, and SpeI are unique, ClaI, SalI, EcoRi, PstI, and HindIII are not unique.

Figure 7:
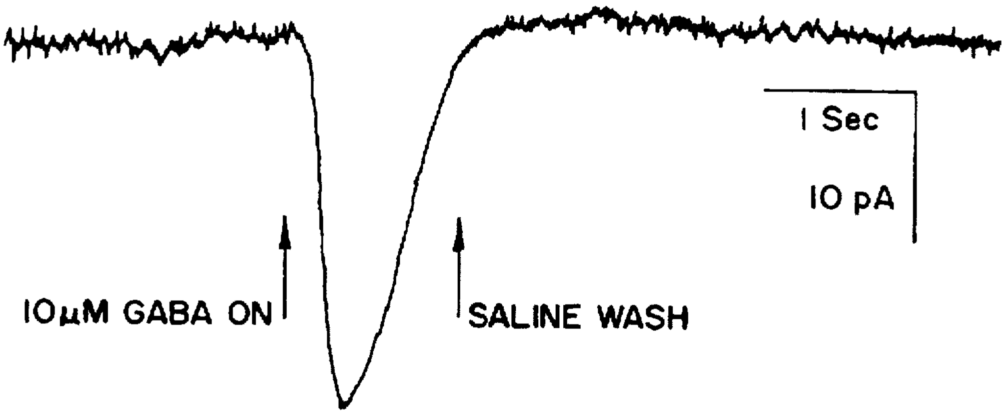
FIG. 7 presents electrophysiological recordings demonstrating a functional GABA gated chloride channel expressed in a permanently transformed cell line.

Drosophila cell line SH1 was transformed with plasmid pIVY17 using lipofectin obtained from GIBCO-BRL following the manufacturer's instructions. Selection of insect cell transformants was accomplished with hygromycin at a concentration of 200 μg/ml. The Heliothis GABA gated chloride channel expression was induced by 10 μM cadmium chloride added to the growth medium for 48 hours prior to electrophysiological readings. Whole cell voltage patch clamping recordings were performed on a number of cell lines as described in Example III. Typical results are presented in FIG. 7 and demonstrate that GABA exhibits the predicted gross functional effect on the GABA gated chloride channel, i.e., flux of chloride ion. This example demonstrates that expression of DNA encoding a lepidopteran GABA gated chloride channel subunit in permanently transformed cell lines results in a functional GABA gated chloride channel.

What is claimed is:

1. An isolated nucleic acid encoding a lepidopteran GABA gated chloride channel subunit comprising the sequence of at least one of SEQ ID NO: 1, SEQ ID NO: 3, nucleotides 115 to 1581 of SEQ ID NO: 1, nucleotides 115 to 1581 of SEQ ID NO: 3, a nucleic acid encoding the polypeptide of SEQ ID NO:2 or a nucleic acid encoding the polypeptide of SEQ ID NO:4.

2. An isolated nucleic acid encoding a lepidopteran GABA gated chloride channel subunit capable of hybridizing at about 50° C., 2x SSC to at least one of the complement of SEQ ID NO: 1, the complement of SEQ ID NO: 3, the complement of a nucleic acid encoding the polypeptide of SEQ ID NO: 2 or the complement of a nucleic acid encoding the polypeptide of SEQ ID NO:4.

3. An isolated nucleic acid having a sequence encoding the amino acid sequence of SEQ ID NO: 2 or SEQ ID NO: 4.

4. An expression vector comprising the isolated nucleic acid of any one of claims 1, 2, or 3.

5. A host cell comprising an expression vector comprising the isolated nucleic acid of claim 1, 3 or 5.

6. The host cell of claim 5 wherein said host cell is a bacterial cell, a yeast cell, an insect cell or a mammalian cell.

7. A Xenopus oocyte comprising the isolated nucleic acid of claim 1, 2 or 3.

8. Recombinant lepidopteran GABA gated chloride channel comprising the amino acid sequence as set forth in SEQ ID NO: 2 or SEQ ID NO: 4.

9. A Xenopus oocyte expressing at least one functional lepidopteran GABA gated chloride channel comprising the amino acid sequence as set forth in at least one of SEQ ID NO: 2 or SEQ ID NO: 4.

10. An insect cell expressing at least one functional recombinant lepidopteran GABA gated chloride channel comprising the amino acid sequence as set forth in at least one of SEQ ID NO: 2 or SEQ ID NO: 4.

11. The cell of claim 10 wherein said cell is an Sf9 cell.

12. A method for preparing a lepidopteran GABA gated chloride channel comprising culturing a host cell comprising the expression vector of claim 4 under conditions suitable for expression.

13. A method for preparing a Xenopus oocyte expressing at least one functional lepidopteran GABA gated chloride channel which comprises injecting a Xenopus oocyte with a nucleic acid encoding, at least one lepidopteran GABA gated chloride channel, wherein the nucleic acid is selected from the group consisting of a nucleic acid having the sequence of SEQ ID NO: 1 or SEQ ID NO: 3 or nucleotides 115 to 1581 of SEQ ID NO: 1 or nucleotides 115 to 1581 of SEQ ID NO: 3, a nucleic acid encoding the polypeptide of SEQ ID NO:2, a nucleic acid encoding the polypeptide of SEQ ID NO:4, a nucleic acid capable of hybridizing at about 50° C., 2x SSC, to the complement of a nucleic acid having SEQ ID NO: 1, a nucleic acid capable of hybridizing at about 50° C., 2x SSC, to the complement of a nucleic acid having SEQ ID NO: 3, a nucleic acid capable of hybridizing at about 50° C., 2X SSC, to the complement of a nucleic acid encoding the polypeptide of SEQ ID NO: 2, and a nucleic acid capable of hybridizing at about 50° C., 2X SSC, to the complement of a nucleic acid encoding the polypeptide of SEQ ID NO: 4 and culturing said oocyte under conditions suitable for expression of said lepidopteran GABA gated chloride channel.

14. A composition comprising a eukaryotic cell membrane containing at least one functional lepidopteran GABA gated chloride channel, encoded by a nucleic acid selected from the group consisting of a nucleic acid having the sequence of SEQ ID NO: 1 or SEQ ID NO: 3 or nucleotides 115 to 1581 of SEQ ID NO: 1 or nucleotides 115 to 1581 of SEQ ID NO: 3, a nucleic acid encoding the polypeptide of SEQ ID NO:2, a nucleic acid encoding the polypeptide of SEQ ID NO:4, a nucleic acid capable of hybridizing at about 50° C., 2x SSC, to the complement of a nucleic acid having SEQ ID NO: 1, a nucleic acid capable of hybridizing at about 50° C., 2x SSC, to the complement of a nucleic acid having SEQ ID NO: 3, a nucleic acid capable of hybridizing at about 50° C., 2X SSC, to the complement of a nucleic acid encoding the polypeptide of SEQ ID NO: 2, and a nucleic acid capable of hybridizing at about 50° C., 2X SSC, to the complement of a nucleic acid encoding the polypeptide of SEQ ID NO: 4.

15. A composition comprising a eukaryotic host cell expressing a functional lepidopteran GABA gated chloride channel, encoded by a nucleic acid selected from the group consisting of a nucleic acid having the sequence of SEQ ID NO: 1 or SEQ ID NO: 3 or nucleotides 115 to 1581 of SEQ ID NO: 1 or nucleotides 115 to 1581 of SEQ ID NO: 3, a nucleic acid encoding the peptide of SEQ ID NO:2, a nucleic acid encoding the peptide of SEQ ID NO:4, a nucleic acid capable of hybridizing at about 50° C., 2x SSC, to the complement of a nucleic acid having SEQ ID NO: 1, a nucleic acid capable of hybridizing at about 50° C., 2x SSC, to the complement of a nucleic acid having SEQ ID NO: 3, a nucleic acid capable of hybridizing at about 50° C., 2X SSC, to the complement of a nucleic acid encoding the polypeptide of SEQ ID NO: 2, and a nucleic acid capable of hybridizing at about 50° C., 2X SSC, to the complement of a nucleic acid encoding the polypeptide of SEQ ID NO: 4.

16. A kit containing a first container containing a recombinant lepidopteran GABA gated chloride channel according to claim 8 in a cell membrane.

17. The kit of claim 16 wherein said cell membrane is a membrane preparation, a freeze dried membrane preparation, an intact cell or an oocyte.

* * * * *

UNITED STATES PATENT AND TRADEMARK OFFICE

CERTIFICATE OF CORRECTION

PATENT NO. : 5,767,261

DATED : June 16, 1998

INVENTOR(S) : Vincent Wingate, et. al.

It is certified that error appears in the above-indentified patent and that said Letters Patent is hereby corrected as shown below:

On The Title Page, [56] References Cited, OTHER PUBLICATIONS:

"instect" should read --insect--

On The Title Page, [56] References Cited, OTHER PUBLICATIONS:

"Receptrors" should read --Receptors--

On The Title Page, [56] References Cited, OTHER PUBLICATIONS:

"inverebrates" should read --invertebrates--

On The Title Page, [56] References Cited, OTHER PUBLICATIONS:

"Boichem." should read --Biochem.--

Signed and Sealed this

Twentieth Day of March, 2001

Nicholas P. Godici

*Attest:*

NICHOLAS P. GODICI

*Attesting Officer* *Acting Director of the United States Patent and Trademark Office*